(12) United States Patent
Marks et al.

(10) Patent No.: US 11,026,708 B2
(45) Date of Patent: Jun. 8, 2021

(54) INTRAVASCULAR THROMBOEMBOLECTOMY DEVICE AND METHOD USING THE SAME

(75) Inventors: Michael P. Marks, Hillsborough, CA (US); Like Que, Livermore, CA (US)

(73) Assignee: ThrombX Medical, Inc., Hillsborough, CA (US)

(*) Notice: Subject to any disclaimer, the term of this patent is extended or adjusted under 35 U.S.C. 154(b) by 0 days.

(21) Appl. No.: 13/543,657

(22) Filed: Jul. 6, 2012

(65) Prior Publication Data

US 2013/0030461 A1    Jan. 31, 2013

Related U.S. Application Data

(63) Continuation-in-part of application No. 13/191,306, filed on Jul. 26, 2011, now abandoned.

(51) Int. Cl.
*A61F 2/01* (2006.01)
*A61B 17/221* (2006.01)
(Continued)

(52) U.S. Cl.
CPC ...... *A61B 17/221* (2013.01); *A61B 17/22032* (2013.01); *A61F 2/013* (2013.01);
(Continued)

(58) Field of Classification Search
CPC .............. A61F 2/013; A61B 17/221; A61B 17/320725; A61B 2017/2212
(Continued)

(56) References Cited

U.S. PATENT DOCUMENTS

| 5,011,488 A | 4/1991 | Ginsburg |
| 5,846,251 A * | 12/1998 | Hart ................. A61B 17/22031 |
| | | 606/127 |

(Continued)

FOREIGN PATENT DOCUMENTS

| CN | 102036611 A | 4/2011 |
| EP | 1 054 635 B1 | 1/2010 |

(Continued)

OTHER PUBLICATIONS

International Search Report dated Nov. 1, 2012 for International Application No. PCT/US2012/048158.
(Continued)

*Primary Examiner* — Anh T Dang
(74) *Attorney, Agent, or Firm* — Knobbe, Martens, Olson & Bear, LLP

(57) ABSTRACT

A device and a method for increasing or restoring a flow in a body lumen are provided. The device and the method may treat conditions related to a stroke, such as an ischemic stroke, by removing an occlusion from a blood vessel and/or reopen a blood vessel. The device may comprise a tubing compartment, a central wire, and an engaging compartment. The engaging compartment may comprise a distal engaging element and a proximal engaging element. A clot or occlusion present in the body lumen such as an artery may be engaged in and/or between the distal and proximal engaging elements. Further, the positions of one or both of the engaging elements and the distance therebetween can be adjusted to ensure the engagement of the clot or occlusion.

7 Claims, 34 Drawing Sheets

(51) Int. Cl.
*A61B 17/22* (2006.01)
*A61B 17/00* (2006.01)

(52) U.S. Cl.
CPC ............... *A61B 2017/00778* (2013.01); *A61B 2017/2215* (2013.01); *A61B 2017/22038* (2013.01); *A61B 2017/22051* (2013.01); *A61F 2002/016* (2013.01); *A61F 2230/008* (2013.01); *A61F 2230/0076* (2013.01); *A61F 2230/0093* (2013.01)

(58) Field of Classification Search
USPC .... 606/159, 200; 623/1.11, 1.12, 1.23, 2.11, 623/23.72
See application file for complete search history.

(56) References Cited

U.S. PATENT DOCUMENTS

| | | | |
|---|---|---|---|
| 5,972,019 | A | 10/1999 | Engelson et al. |
| 5,984,957 | A | 11/1999 | Laptewicz, Jr. et al. |
| 6,096,053 | A | 8/2000 | Bates |
| 6,248,128 | B1 | 6/2001 | Berry et al. |
| 6,458,139 | B1* | 10/2002 | Palmer ............... A61B 17/221 606/113 |
| 7,029,488 | B2 | 4/2006 | Schonbolz et al. |
| 8,858,497 | B2 | 10/2014 | Di Palma et al. |
| 9,204,887 | B2 | 12/2015 | Cully et al. |
| 2002/0091407 | A1* | 7/2002 | Zadno-Azizi et al. ....... 606/200 |
| 2002/0123765 | A1 | 9/2002 | Sepetka et al. |
| 2003/0078614 | A1 | 4/2003 | Salahieh et al. |
| 2003/0163158 | A1 | 8/2003 | White |
| 2003/0176886 | A1* | 9/2003 | Wholey ................. A61F 2/013 606/200 |
| 2004/0260333 | A1 | 12/2004 | Dubrul et al. |
| 2005/0113862 | A1 | 5/2005 | Besselink et al. |
| 2006/0155305 | A1* | 7/2006 | Freudenthal ......... A61B 17/221 606/114 |
| 2007/0100422 | A1* | 5/2007 | Shumer .................... A61F 2/95 623/1.11 |
| 2008/0097401 | A1 | 4/2008 | Trapp et al. |
| 2008/0114439 | A1 | 5/2008 | Ramaiah et al. |
| 2008/0262487 | A1 | 10/2008 | Wensel |
| 2009/0054918 | A1 | 2/2009 | Henson |
| 2009/0105722 | A1 | 4/2009 | Fulkerson et al. |
| 2009/0105737 | A1 | 4/2009 | Fulkerson et al. |
| 2009/0192485 | A1 | 7/2009 | Heuser |
| 2009/0198269 | A1 | 8/2009 | Hannes et al. |
| 2009/0221967 | A1 | 9/2009 | Thommen et al. |
| 2009/0292297 | A1 | 11/2009 | Ferrere |
| 2009/0299393 | A1* | 12/2009 | Martin ................. A61B 17/221 606/159 |
| 2010/0004726 | A1 | 1/2010 | Hancock et al. |
| 2010/0114017 | A1 | 5/2010 | Lenker et al. |
| 2010/0268265 | A1 | 10/2010 | Krolik et al. |
| 2011/0202088 | A1 | 8/2011 | Eckhouse et al. |
| 2012/0059356 | A1 | 3/2012 | Di Palma et al. |
| 2012/0165859 | A1* | 6/2012 | Eckhouse ............ A61B 17/221 606/200 |
| 2013/0030460 | A1 | 1/2013 | Marks et al. |
| 2013/0030461 | A1 | 1/2013 | Marks et al. |
| 2013/0345739 | A1 | 12/2013 | Brady et al. |
| 2014/0046359 | A1 | 2/2014 | Bowman et al. |
| 2014/0062161 | A1 | 2/2014 | Culley et al. |

FOREIGN PATENT DOCUMENTS

| | | |
|---|---|---|
| EP | 1 629 784 B1 | 1/2010 |
| EP | 1 667 588 B1 | 1/2010 |
| JP | 2003033359 A | 2/2003 |
| JP | 2005160648 A | 6/2005 |
| WO | 02/055146 A1 | 7/2002 |
| WO | 2007/004221 A1 | 1/2007 |
| WO | WO 2007/004221 A1 | 1/2007 |
| WO | WO 2009/076482 A1 | 6/2009 |
| WO | 2011/006013 A1 | 1/2011 |
| WO | WO 2012/162437 A1 | 11/2012 |

OTHER PUBLICATIONS

International Search Report dated Jun. 2, 2015 for PCT/US2015/018752.
Restriction Requirement dated Feb. 4, 2013 for U.S. Appl. No. 13/191,306.
Office Action dated May 10, 2013 for U.S. Appl. No. 13/191,306.
Final Office Action dated Dec. 17, 2013 for U.S. Appl. No. 13/191,306.
Advisory Action dated May 5, 2014 for U.S. Appl. No. 13/191,306.
Office Action dated Aug. 26, 2014 for U.S. Appl. No. 13/191,306.
Final Office Action dated Jan. 27, 2015 for U.S. Appl. No. 13/191,306.
Extended European Search Report dated Dec. 23, 2014 for EP 12 81 7411.
Office Action dated Jan. 23, 2015 for CN201280036998.X.
International Report on Patentability dated Nov. 21, 2013 for PCT/US2012/048158.
Decision of Rejection dated Sep. 27, 2016 in corresponding Chinese Application No. 201280036998.X, filed Jan. 24, 2014.
U.S. Appl. No. 13/191,306, filed Jul. 26, 2011, Intravascular Thromboembolectomy Device and Method Using the Same.
U.S. Appl. No. 13/543,657, filed Jul. 6, 2012, Intravascular Thromboembolectomy Device and Method Using the Same.
U.S. Appl. No. 15/190,047, filed Jun. 22, 2016, Intravascular Thromboembolectomy Device and Method Using the Same.
U.S. Appl. No. 14/638,994, filed Mar. 4, 2015, Intravascular Thromboembolectomy Device Comprising a Plurality of Clot Engaging Elements and Method Using the Same.
Second Office Action dated Sep. 18, 2015 in Chinese Application No. 201280036998.X, filed Jan. 24, 2014.
Third Office Action dated Mar. 24, 2016 in Chinese Application No. 201280036998.X, filed Jan. 24, 2014.
Office Action dated Jun. 7, 2016 in Japanese Application No. 2014-522968, filed Jan. 6, 2014.
Notice of Allowance dated Sep. 20, 2016 in Japanese Application No. 2014-522968, filed Jan. 6, 2014.
Supplementary European Search dated Jun. 20, 2017 in corresponding European Application 15758875.7, filed Aug. 26, 2016.
Office Action dated Jan. 13, 2017 in U.S. Appl. No. 15/190,047.
Final Office Action dated Jun. 5, 2017 in U.S. Appl. No. 15/190,047.
Office Action dated Aug. 27, 2015 in U.S. Appl. No. 13/191,306.

\* cited by examiner

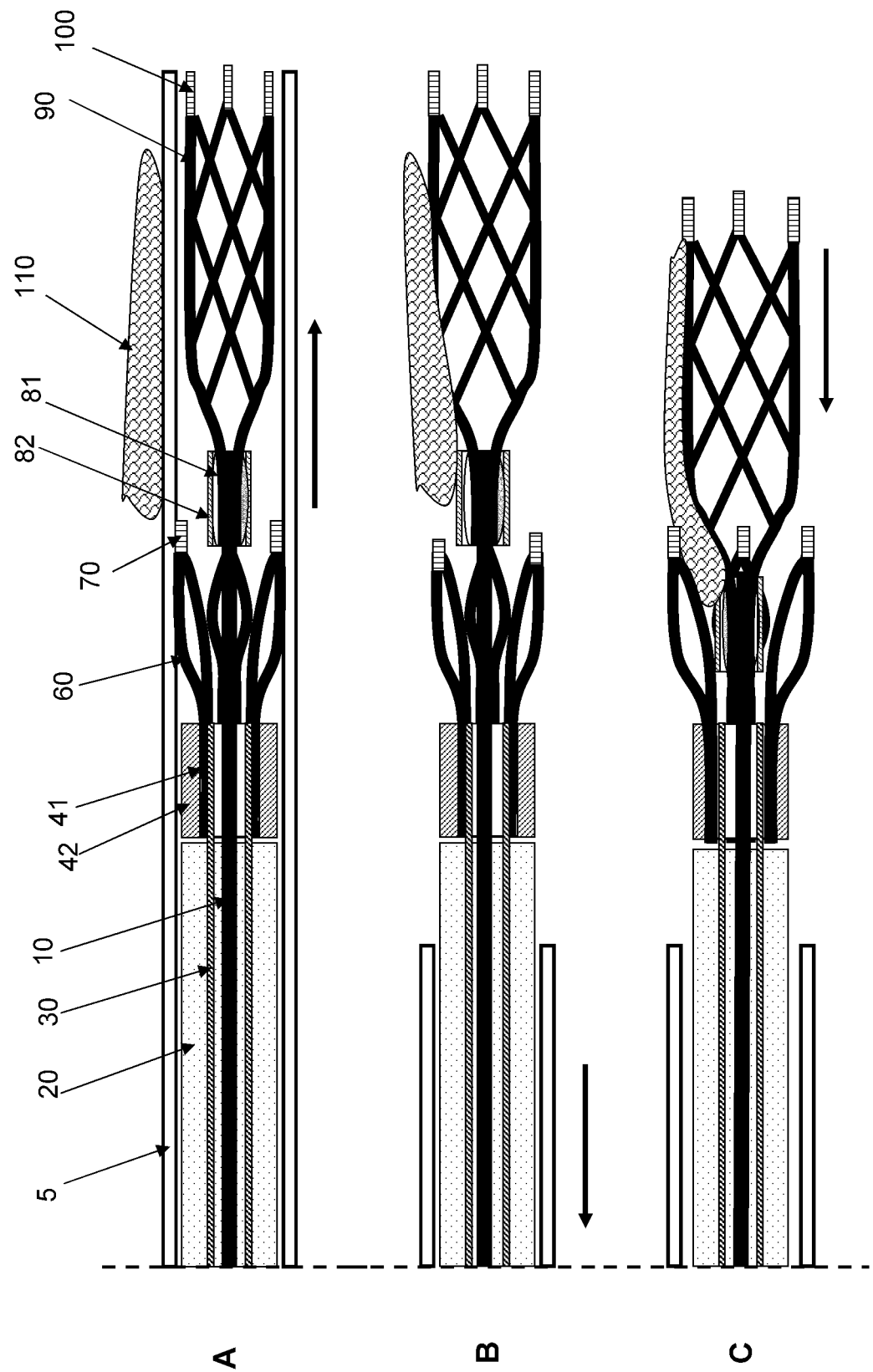

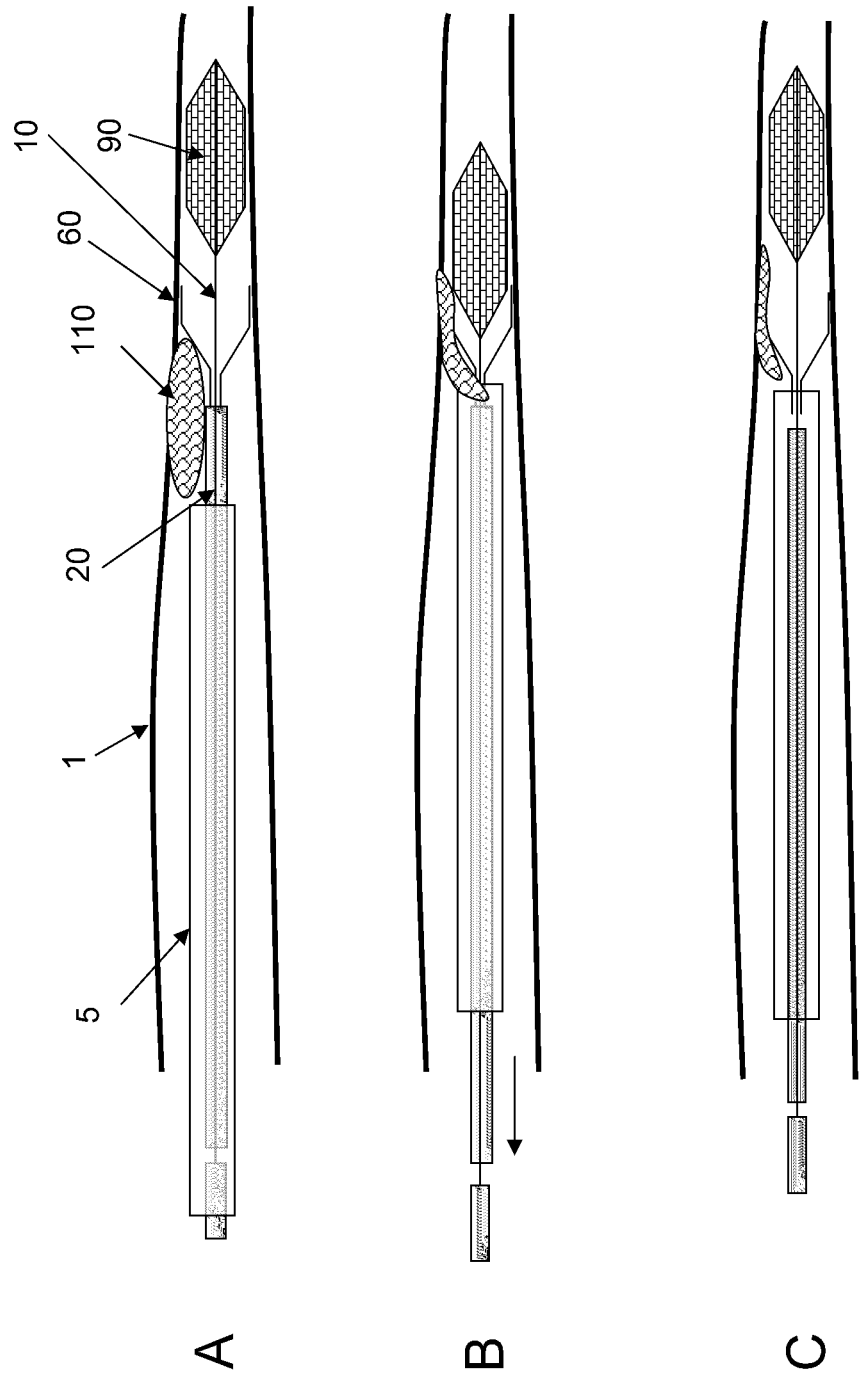

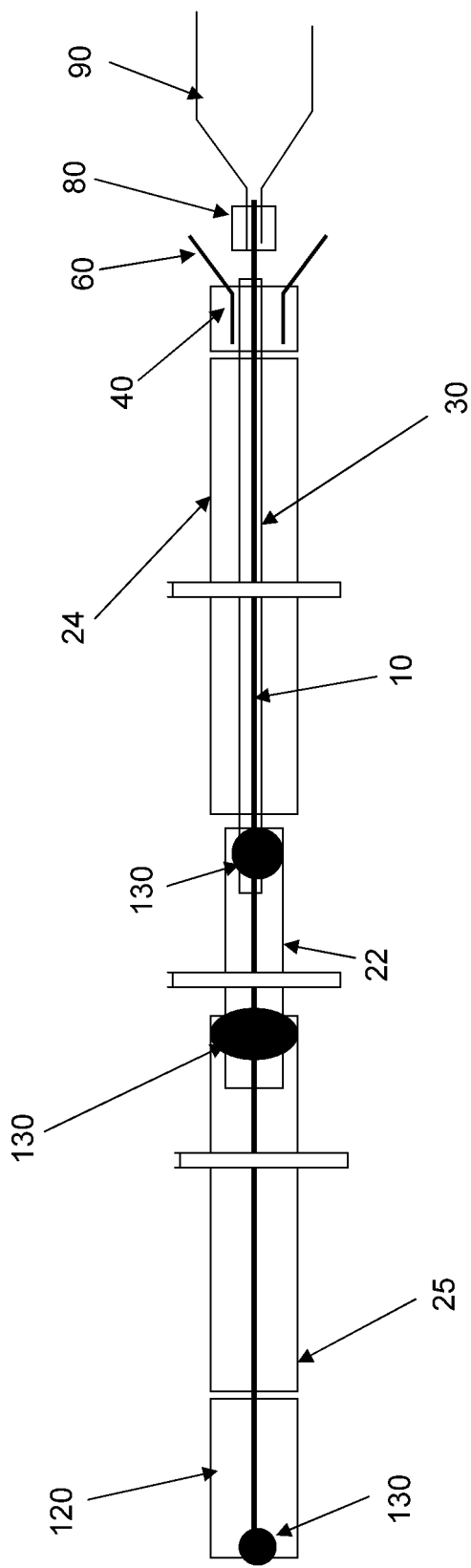

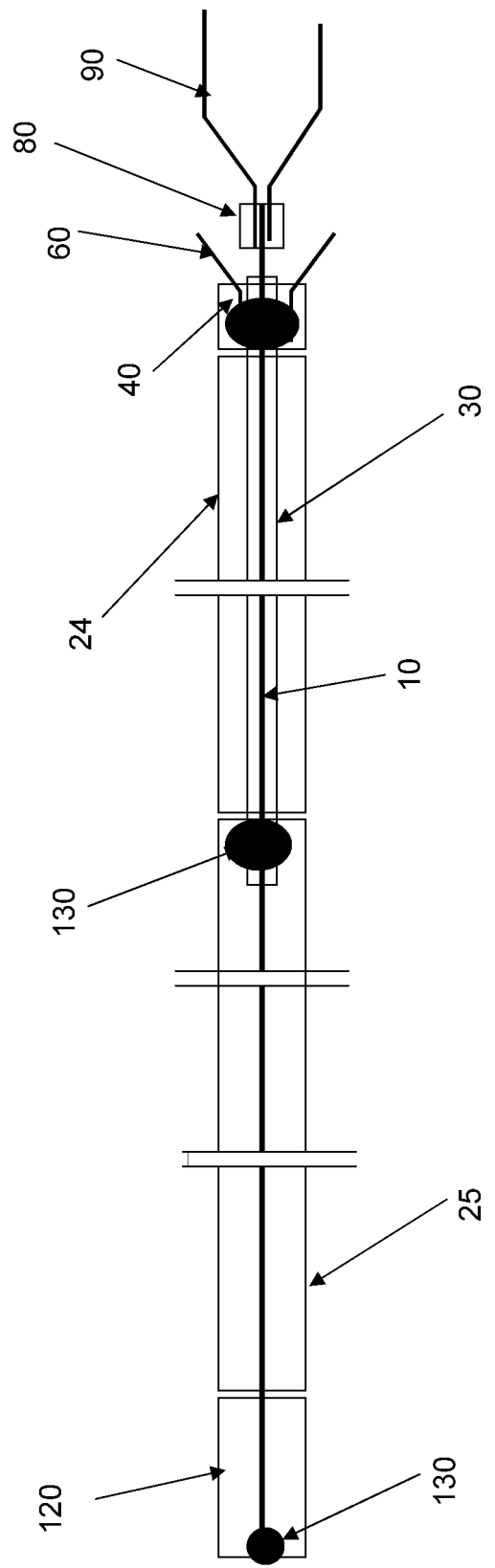

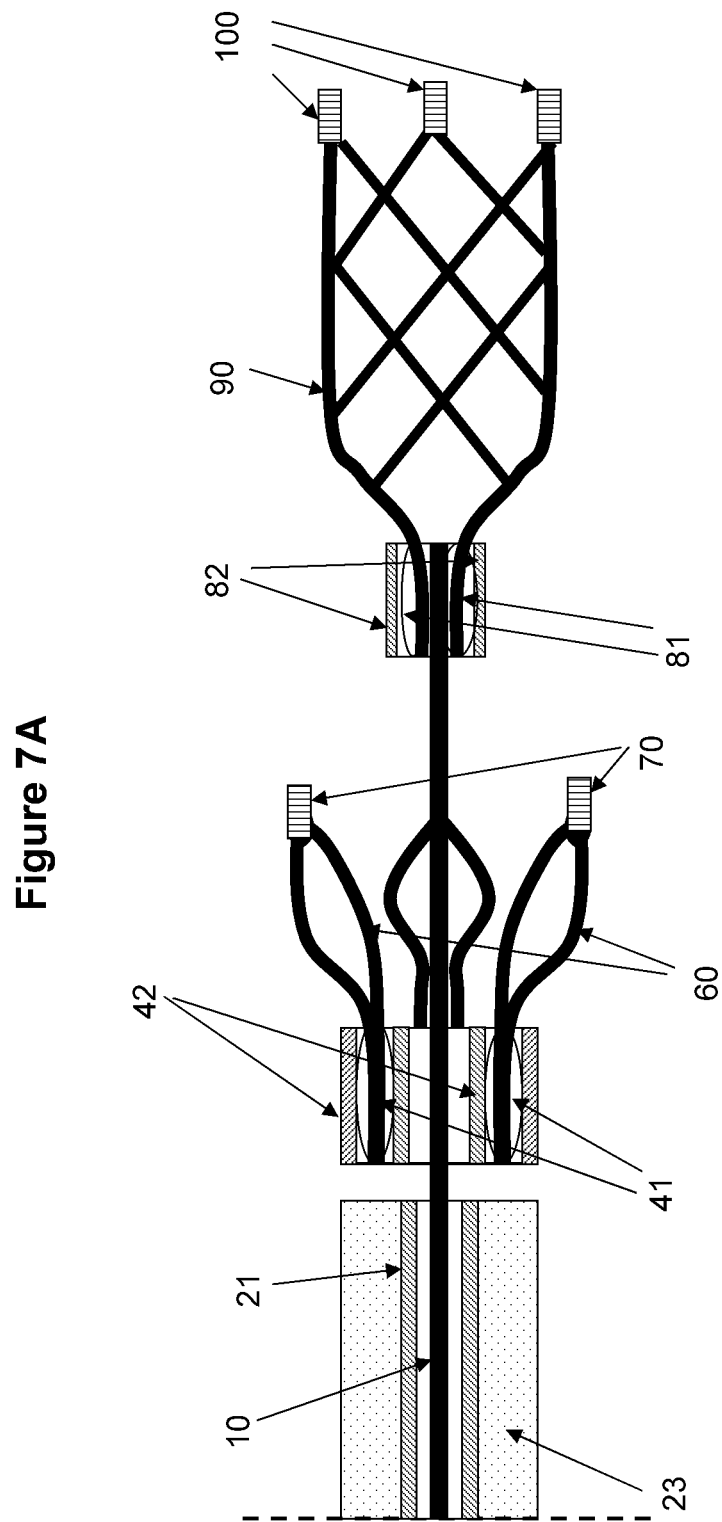

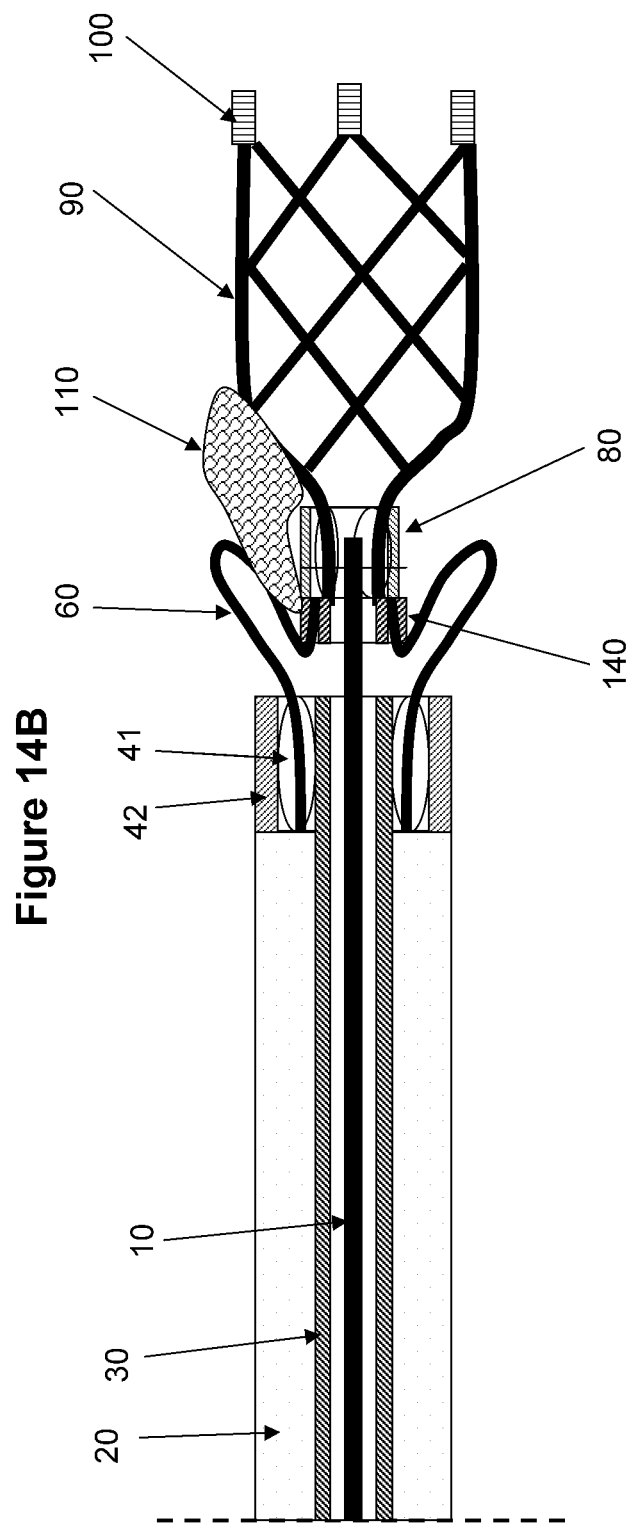

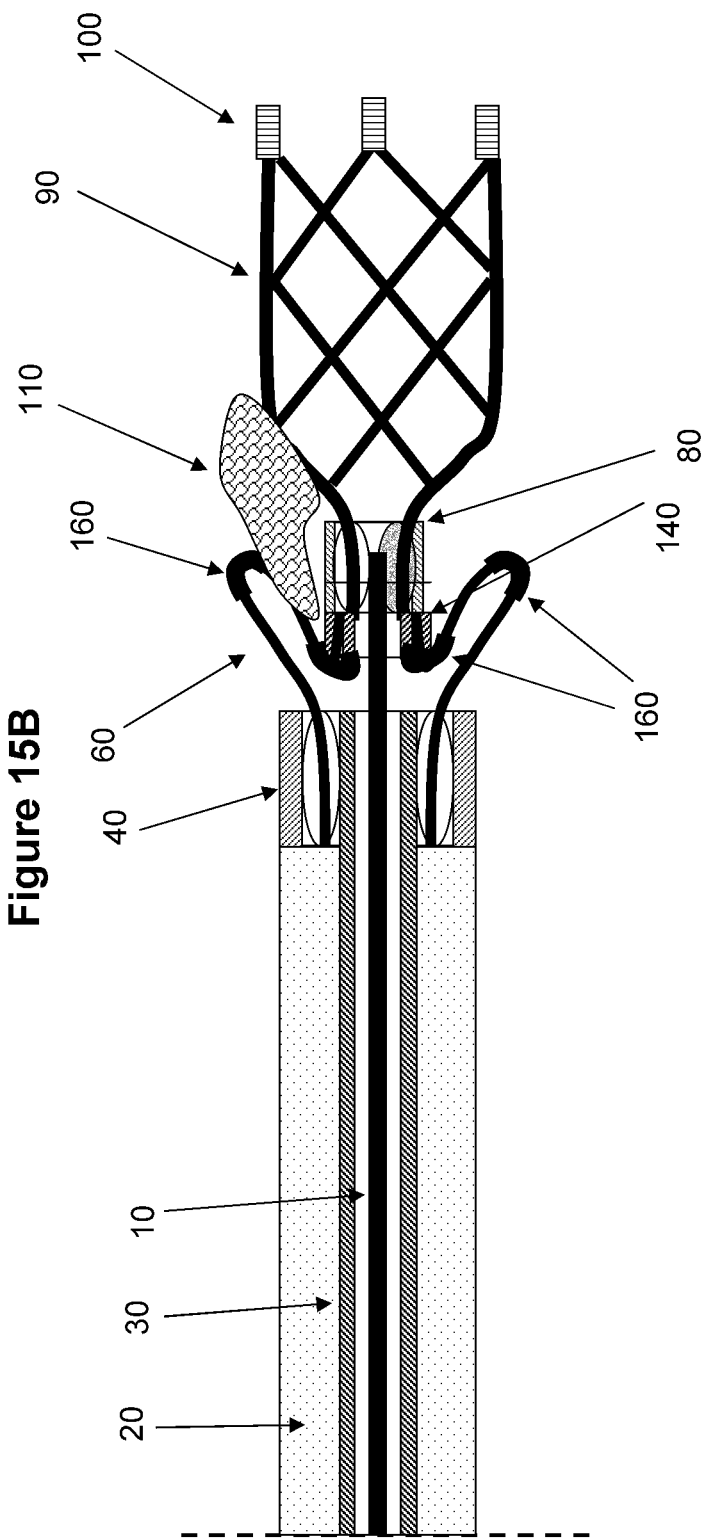

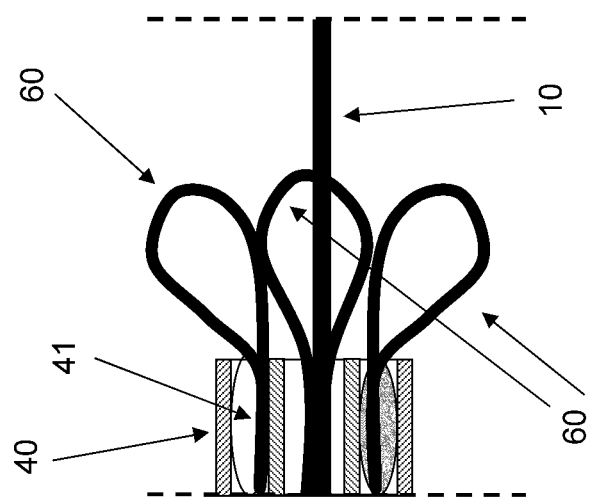

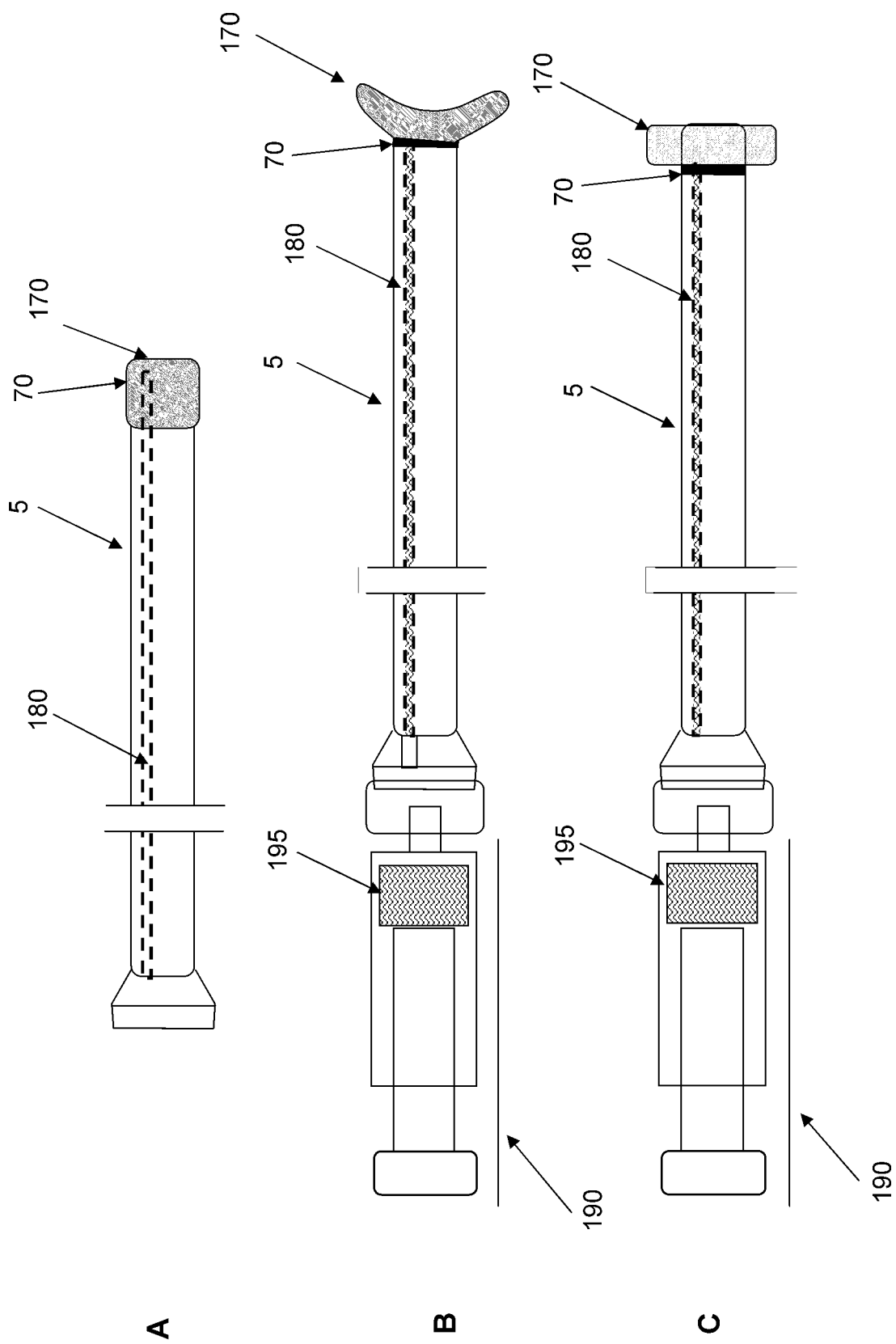

INTRAVASCULAR THROMBOEMBOLECTOMY DEVICE AND METHOD USING THE SAME

CROSS-REFERENCE TO RELATED APPLICATIONS

This application is a Continuation in Part of U.S. application Ser. No. 13/191,306, filed Jul. 26, 2011, which is incorporated by reference in its entirety.

BACKGROUND OF THE INVENTION

Field of the Invention

The present disclosure is generally related to a device used in a body lumen and a method of using the same.

Description of the Related Art

A variety of disease conditions can be caused, at least in part, by blockage or occlusions of blood vessels. A well-known example of such conditions includes, but is not limited to stroke. Other such conditions include a myocardial infarction, limb ischemia, occlusions of vascular grafts and bypasses, and venous thromboses.

A stroke is often referred as a "brain attack." It often results in rapid and significant loss of brain function due to disturbance in the blood supply to the brain. As a result, inabilities in movement, use of language, vision and many other biological functions may be temporarily or irreversibly impaired. Strokes are either hemorrhagic (due to bleeding) or ischemic (due to inadequate blood supply). The majority of strokes are ischemic. It is estimated that about 700,000 ischemic strokes occur in the United States annually. The major causes of an ischemic stroke include thrombosis (clotting) in a blood vessel supplying the brain or an embolus from another source such as the heart going to a blood vessel supplying the brain. Sometimes a thrombosis occurs where there is a pre-existing stenosis of blood vessels in the brain, usually form atherosclerotic disease.

Treatments for acute ischemic stroke are concentrated on re-establishing blood flow to the brain as quickly as possible. They include the use of a drug such as tissue plasminogen activator (tPA), a thrombolytic agent (clot-busting drug). More recently devices such as the Merci thrombectomy device (Concentric Medical, Mountain View, Calif.) and the Penumbra suction thrombectomy catheter (Penumbra, Inc., Alameda, Calif.) and the Solitaire thrombectomy device (ev3 Neurovascular, Irvine, Calif.) have been approved by the Food and Drug Administration for thrombectomy in acute stroke. These devices do not always achieve complete recanalization. Sometimes they fail to open the vessel at all or may only partially open the vessel. They also may take some time to work, with multiple passes of the devices into the intracranial circulation needed before the vessel is reopened. In addition they may fragment the clot and allow some clot to go out more distally in the cerebral circulation. There is a need for devices with high rates of complete recanalization, with complete clot capture, performed in a more rapid manner.

SUMMARY OF THE INVENTION

According to one aspect of the invention, a device for use in a body lumen is provided. The device may comprise a microcatheter comprising a distal end and a proximal end, a tubing compartment, a central wire, and an engaging compartment. The engaging compartment may comprise a proximal engaging element, and a distal engaging element. The distal engaging element may be an expandable element that is associated with the central wire, and a distance between the proximal engaging element and the distal engaging element is adjustable.

In some embodiments, the distal engaging element of the foregoing device may comprise a plurality of wires or struts forming a stent. The distal engaging element may be fixed with the central wire extending to a proximal end of the device, thereby a location of the distal engaging element in the body lumen is controlled by movement of the central wire.

In some other embodiments, the proximal engaging element of the foregoing device may be an expandable element comprising a plurality of wires or struts and can expand into a funnel or cone shaped structure. The proximal engaging element may be associated with the central wire and moves along the central wire. In some alternative embodiments, the proximal engaging element may be fixed with the tubing compartment extending to a proximal end of the device, thereby a location of the proximal engaging element in the body lumen is controlled by movement of the tubing compartment. In still some alternative embodiments, the proximal engaging element may not be fixed with the tubing compartment and configured to freely move along the central wire.

In still some other embodiments, the proximal engaging element may be located at the distal end of the microcatheter. In certain embodiments, the proximal engaging element may not be an integral part of the microcatheter and fixed at the distal end of the microcatheter.

In still some other embodiments, the proximal engaging element may be an inflatable or engaging element. In certain embodiments, the proximal engaging element may be an integral part of the microcatheter.

In still some other embodiments, the proximal engaging element of the foregoing device may comprise a portion of the distal end of the microcatheter, said portion being configured to change a shape depending on a pressure applied to the distal end of the microcatheter. In certain embodiments, the proximal engaging element may comprise a portion of the distal end of the microcatheter comprising a microcather tip and a layer of thin tubing that covers the microcatheter tip, wherein at least part of said proximal engaging element may be configured to change a shape when a layer of thin tubing is removed.

In still some other embodiments, the tubing compartment of any of the foregoing device may comprise a pusher tubing and a connecting tubing.

In still some other embodiments, the tubing compartment of the device may be made from one piece of tubing with variable stiffness such that a distal end of the tubing compartment may be soft and flexible so the device can pass tortuous anatomy while a proximal end of the tubing compartment may be stiff to enhance pushability of the device.

In still some other embodiments, the central wire of any of the device may comprise a wire, a cable, or a braid. The distance between the proximal engaging element and the distal engaging element may be adjustable approximately in range of 0 to 50 mm.

In still some other embodiments, the proximal engaging element of any of the device may comprise a distal end facing the distal engaging element, said distal end of the proximal engaging element being bended, rounded, or smoothed. In alternative embodiments, the proximal engaging element of the device may comprise a distal end facing the distal engaging element, said distal end of the proximal engaging element being configured not to be in direct contact with a surface of the body lumen.

According to another aspect of the invention, a method of removing at least part of an occlusion from a first location in a body lumen is provided. The method may comprise introducing the device according to Claim 1 into the body lumen, locating the device at about the first location, engaging the at least part of the occlusion with the engaging element, and removing the engaged occlusion from the first location.

In some embodiments, the engaging step of the method may comprise adjusting the position of one or both of the proximal engaging element and the distal engaging element so as to engage at least part of the occlusion with the proximal engaging element and/or the distal engaging element. In some other embodiments, the engaging step of the method may comprise adjusting the distance between the proximal engaging element and the distal engaging element so as to engage the at least part of the occlusion between the proximal engaging element and the distal engaging element.

In some other embodiments, the method may further comprise, after engaging, locking the position of one or both of the proximal engaging element and the distal engaging element. In certain embodiments, in the engaging step of the foregoing method, at least part of the occlusion is engaged with any component selected from the group consisting of the surface of the body lumen, the microcatheter, the tubing compartment, the proximal engaging element, the distal engaging element, and any combinations thereof.

BRIEF DESCRIPTION OF THE DRAWINGS

FIG. 1 shows a non-limiting illustrative embodiment of a device according to the invention. FIG. 1A' shows an embodiment where the proximal engaging element is made from a tubing.

FIG. 2 shows a non-limiting illustrative embodiment of a method for removing an occlusion or part of an occlusion from a body lumen according to the invention.

FIG. 5 shows a non-limiting illustrative embodiment of a system according to the invention.

FIG. 6 shows another non-limiting illustrative embodiment of a system according to the invention.

FIG. 7 shows another non-limiting illustrative embodiment of a device according to the invention. FIG. 7A shows an open status of the device and FIG. 7B shows a closed status of the device.

FIG. 11 shows still another non-limiting illustrative embodiment of a device according to the invention.

FIG. 13 shows still another non-limiting illustrative embodiment of a device according to the invention.

FIG. 14 shows still another non-limiting illustrative embodiment of a device according to the invention. FIG. 14A shows an open status of the device and FIG. 14B shows a closed status of the device where an occlusion is engaged with the device.

FIG. 15 shows still another non-limiting illustrative embodiment of a device according to the invention. FIG. 15A shows an open status of the device and FIG. 15B shows a closed status of the device where an occlusion is engaged with the device.

FIG. 16 shows still another non-limiting illustrative embodiment of a device according to the invention. Especially, the figure illustrates an alternative embodiment of the proximal portion a device.

FIG. 17 shows still another non-limiting illustrative embodiment of a device according to the invention. Especially, the figure illustrates an embodiment where a microcatheter comprises a tip that is transformable into a different shape.

REFERENCE NUMERALS FOR DESIGNATING MAIN COMPONENTS IN THE DRAWINGS

Figure 1A:
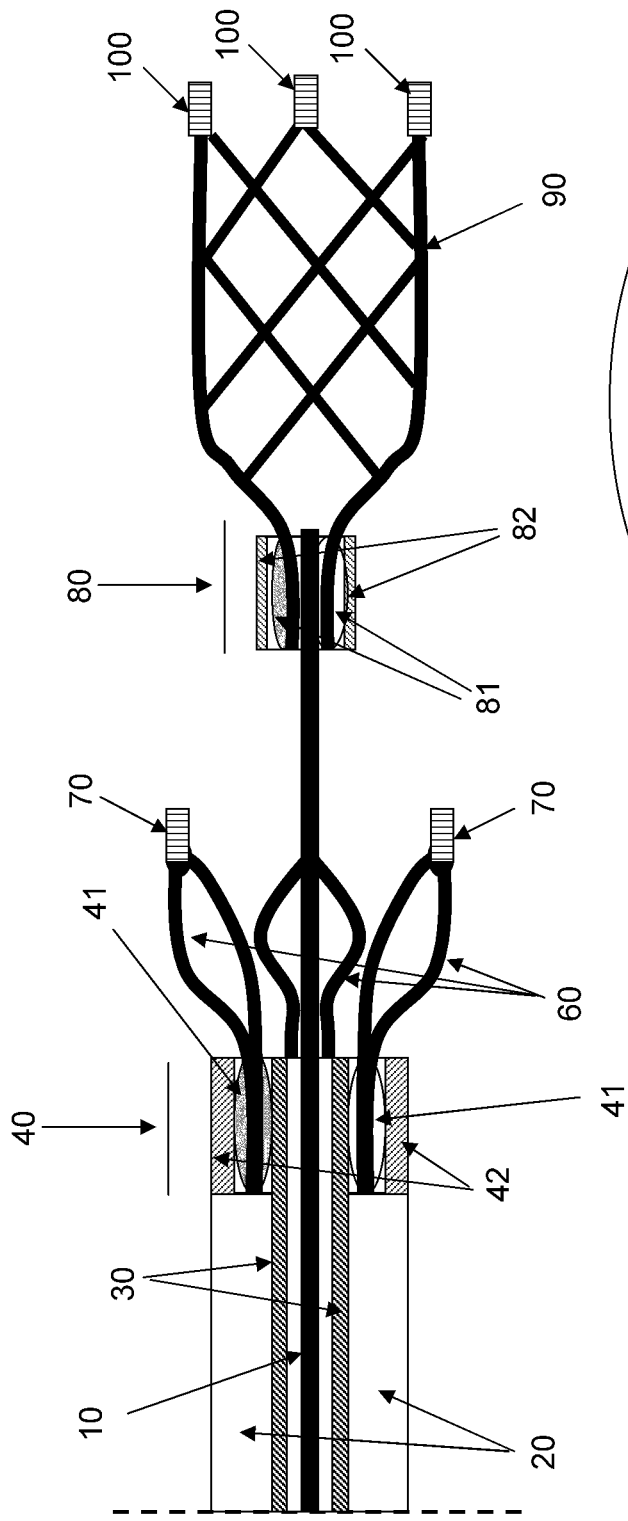
FIG. 1A shows an open status of the device.

1: Body lumen surface
5: Microcatheter

10: Central wire
20: Pusher tubing
21: Inner pusher tubing
22: Middle pusher tubing
23: Outer pusher tubing
24: Distal pusher tubing
25: Proximal pusher tubing
30: Connecting tubing
40: Proximal element connector
41: Proximal element joining media
42: Outer proximal element connector
60: Proximal engaging element
70: Proximal element marker
80: Distal element connector
81: Distal element joining media
82: Outer distal element connector
90: Distal engaging element
100: Distal element marker
110: Occlusion or clot
120: Distal component control handle
130: Joint
140: Distal connector of proximal component
150: Connecting wire of proximal component
160: Segment connector of proximal component
170: Inflatable or expandable element
180: Injection channel
190: Syringe
195: Injection liquid
200: Transformable microcatheter distal tip
210: Outer sheath
220: Wire
230: Channel

DETAILED DESCRIPTION OF THE EMBODIMENTS

The present disclosure is generally related to a device used in a body lumen, such as a blood vessel, and a method of using the same. In some embodiments, the device may be positioned in the body lumen to dilate the lumen and/or remove an occlusion from the lumen. While the device is in the portion of the body lumen that is in need of treatment, an operator can maneuver the device to expand the lumen and/or engage the occlusion.

Some aspects of the present invention provide a device and a method that are configured to treat conditions in blood vessels which include, but are not limited to, a stroke. In some embodiments, the device and the method are configured to treat conditions related to an ischemic stroke by removing an occlusion from a blood vessel and/or reopen a blood vessel with some underlying stenosis to resume blood flow therein.

Non-limiting examples of blood vessels may include, an artery, a vein and surgically implanted grafts and bypasses serving as components of the circulatory system.

The term "occlusion" or "clot" generally includes any matter partially or completely obstructing a lumen of the blood vessel. The occlusion slows or obstructs a flow (e.g. a stream of blood or any other biological fluid) running through the lumen. Examples of the occlusion may include blood clots and atherosclerotic plaques present in the vessel as well as fat or foreign bodies.

The term "stroke" generally includes a condition(s) that is in part caused due to disturbance in blood supply to a brain. The disturbance can be caused by blockage (e.g. ischemic stroke) and/or hemorrhage (e.g. hemorrhagic stroke) of blood. In particular, an ischemic stroke can be caused due to partial or substantial occlusion of blood vessel. Treatment of the ischemic conditions can be applied to blood vessels present in the brain as well as in other tissues such as the heart. Accordingly, the device and method disclosed in this application are not limited to use in any particular organs but can be applied to any blood vessel of the body that needs dilation of the lumen or removal of occlusion to restore blood flow. In addition, the device and method according to the present invention can be used to treat venous occlusions which may result in other conditions besides ischemia.

The device can be introduced into the blood vessel through a catheter. The "catheter" generally includes a tubular structure that can be inserted into a body lumen, thereby allowing administration of a device and/or chemicals to a body area that needs treatment. The term "microcatheter" may refer to a catheter that is configured to be administered in a relatively small body lumen such as blood vessels.

The term "tubing" generally refers to a tubular shaped object such as a conduit which may comprise a hollow space (e.g. cylindrical) used to hold and/or conduct a contained objected. Tubing can be made of various materials such as metal, plastic, glass, or any combinations thereof.

The term "wire" generally refers to a metallic or non-metallic object drawn out into the form of a thin flexible thread or rod. The length and thickness of a wire can be highly variable from nanometer scales to meter scales.

The term "stent" generally refers to a tubular support placed temporarily or permanently inside a body lumen, e.g. blood vessel, canal, or duct to aid healing or relieve an obstruction. A stent may be made of one or more wires. In some occasions, a stent may be in form of a strut, which generally refers to a rod or bar forming part of a framework and designed to resist compression. In some other occasions, a stent may be in form of wire web or wire mesh.

Furthermore, many different modifications and alternations, which should be obvious to a person with ordinary skill in the art, can also be done without affecting the scope of the invention to properly serve the specific treatment conditions. Therefore, not only the examples disclosed in this application but also such an obvious modification and alteration should also be included in the scope of the invention.

One aspect of the present invention is related to a device for use in a blood vessel comprising a microcatheter, a central wire, a tubing component, and an engaging component/compartment. The engaging component/compartment may comprise a distal engaging element and a proximal engaging element. In some embodiments, the distal engaging element may be associated with the central wire. One or both of the proximal and distal engaging elements may be engaging element(s). In certain embodiments, the distance between the distal and proximal engaging elements is adjustable. The distance between the proximal and distal engaging elements can be adjusted approximately from 0 to 50 mm in at least some embodiments. In certain embodiments, the distance between the proximal and distal engaging elements may be adjusted approximately 0 mm, 5 mm, 10 mm, 15 mm, 20 mm, 25 mm, 30 mm, 35 mm, 40 mm, 45 mm, and 50 mm, and any range there between. In alternative embodiments, the distance between the proximal and distal engaging elements may be adjusted to be more than 50 mm.

In some embodiments, the device can be introduced into a blood vessel. The sizes of blood vessels vary enormously, from a diameter of about 0.03 inch (about 1 mm) in smaller arteries and veins to 1.0 inch (about 25 mm) in larger arteries. Accordingly, in some embodiments, the diameter of the device may range from approximately 0.01 inch (about 0.25 mm) to 1.0 inch (about 25 mm). Also, the diameter of a single device may vary during the operation as the engaging compartment gets opened (or expanded) or closed (or collapsed).

In some embodiments, the device further comprises a central wire. The central wire may pass through the tubing component and move freely there through. In certain embodiments, the control wire is associated with the engaging compartment. More particularly, the central wire may be associated with the distal engaging element and the proximal engaging element. Association generally refers to any type of connection between two objects. Association includes fixation in that when two objects are associated, movement of one object would be hindered by another object. In other words, once the two objects are associated in a way of fixation, movement of two objects would be synchronized. However, association does not necessarily indicate fixation of one object to another. Accordingly, when two objects are associated but not in a state of fixation, movement of one object with respect to the other object would not be hindered. Therefore, the distal engaging element and the proximal engaging element, both of which are associated with the central wire, may mover freely along the central wire, in at least some embodiments.

According to certain embodiments, the central wire is fixed or joined with the distal engaging element. In some occasions, the proximal end of the distal engaging element may be joined to the distal end of the central wire. The association (i.e. connection) between the central wire and the distal engaging element may be done via various ways such as welding, gluing, or clipping. In some embodiments, the joint between the central wire and the distal engaging element is covered by a distal element connector. Alternatively, no coverage would be provided to surround the connected control wire and the distal engaging element.

In some embodiments, the central wire may comprise or in be in the form of a wire, braid, or cable. Various materials can be used to manufacture the central wire, which may include metal and non-metal materials. Some non-limiting examples of metal materials for the central wire may comprise nickel, titanium, stainless steel, cobalt, chrome and any alloys of the foregoing such as Nitinol (NiTi), or Cobalt Chromium alloys. In addition, any polymers or plastics which have desired properties of being the central wire can be used for production of the same. Polymers include, but not limited to, Polyimide, PEEK (Polyether ether ketone), Nylon, PTFE (polytetrafluoroethylene), PET (Polyethylene terephthalate), Polypropylene, etc. Polymer coated metal including but not limited to, PTFE coated Stainless Steel, or PTFE coated NiTi can also be used as a central wire. Also hydrophilic coating would be applicable. Such coating can be applicable in part to reduce friction between the central wire and the tubing compartment(s). The central wire can also be made of composite materials, such as PTFE or FEP (Fluorinated ethylene propylene) tubing over NiTi wire, or PTFE or FEP tubing over Stainless Steel etc. The diameter of the central wire may range approximately from 0.001 inch to 0.25 inch. In certain embodiments, the diameter of the central wire may be about 0.001, 0.002, 0.003, 0.004, 0.005, 0.006, 0.007, 0.008, 0.009, 0.011, 0.012, 0.013, 0.014, 0.015, 0.016, 0.017, 0.018, 0.019, 0.020, 0.021, 0.022, 0.023, 0.024 and 0.025 inch. Alternatively, the diameter of the central wire may be more than 0.025 inch.

The term "engaging compartment" generally includes a structure that can be compressed into small diameter and inserted into a body lumen and, upon releasing compression, expands to a larger diameter to recanalize the blocked vessel or counteract localized flow constriction either by opening the vessel or removing at least part of the occlusion. The engaging compartment may comprise a distal engaging element and a proximal engaging element. The distal and proximal engaging elements can be a braid structure in at least some embodiments. They can also be made through laser cut hypo-tubes, or photo etched sheet materials. Heat treatment may be needed to set them into the desired shape, e.g. cone shape or cylinder shapes.

In some embodiments, the engaging elements may comprise a stent made from tubing or sheet materials. In some other embodiments, the engaging elements may comprise a plurality of wires which can be formed into a mesh. In some occasions, the distal end of the distal engaging element may be closed as seen in FIG. 1C. Alternatively, the distal end of the distal engaging element may stay opened as seen in FIG. 1A.

The distal engaging element can be made of metal materials. Some non-limiting examples of such metal materials for the distal engaging element include nickel-titanium (NiTi) alloy, stainless steel, titanium and its alloys, and cobalt chrome (CoCr) alloys. Alternatively, any polymers or plastics which have desired properties for a distal engaging element can be used. In some embodiments, the distal engaging element is made of flexible material(s). In further alternative examples, the distal engaging element can be constructed using two or more different materials, such as polymer coated metal materials.

In some embodiments, a diameter of the distal engaging element may vary from approximately 1 to 8 mm at its expanded state. In certain embodiments, the diameter of the distal engaging element at its expanded state may be approximately 1 mm, 2 mm, 3 mm, 4 mm, 5 mm, 6 mm, 7 mm, and 8 mm or any range therebetween. In some other embodiments, a length of the distal engaging element may vary from approximately 10 to 40 mm. In certain some embodiments, the length of the distal engaging element may be approximately 10 mm, 15 mm, 20 mm, 25 mm, 30 mm, 35 mm, and 40 mm or any range therebetween. Further, in alternative embodiments, the length of the distal engaging element may be more than 40 mm.

The distal engaging elements are in general flexible and with elastic or super-elastic property. Thus the distal engaging element may be varied in its shape. The distal engaging element, typically comprise at least two different configurations which are referred to a "collapsed (i.e. folded or closed)" configuration and a "relaxed (i.e. unfolded or open)" configuration. The collapsed configuration of the distal engaging element generally represents a status in which the outer radius of the distal engaging element becomes minimized. When the distal engaging element is in a microcatheter, the distal engaging element is in its collapsed configuration. When the distal engaging element is pushed out of microcatheter and if there is no compressive force constraining it, the distal engaging element is in its relaxed status. In some embodiments, the distal engaging element may comprise a stent that is self-expandable. Accordingly, once the stent is pushed out of the microcatheter or the microcatheter is withdrawn leaving the stent distal to the microcatheter, the stent is not constrained and it will be expanded on its own. Due to its flexible property, the distal engaging element may be easily placed into the microcatheter by gently pulling or pushing the same toward the microcatheter.

In accordance with some embodiments of the invention, the proximal engaging element may comprise one or more wires made from tubing or sheet material(s). In some other embodiments, the proximal engaging element may comprise one or more wires which can be formed into a basket-like form, e.g. as shown in FIG. 1. Alternatively, the proximal engaging element can be manufactured in many shapes or forms. For example, the distal end of the proximal engaging element, which may face toward the body lumen surface, may be modified in order to reduce any damage to the surface of the body lumen. Accordingly, the distal end of the proximal engaging element has been substantially smoothened so that even in direct contact with the proximal engaging element the body lumen would remain largely undamaged. Also, the distal end of the proximal engaging element would be curved, e.g. as shown in FIG. 11, so that the pointed end would not be in direct contact with the body surface. Further, the shape or form of a proximal engaging element can be varied during the operation. Therefore, in certain embodiments the distal end, more particularly, the distal tip of the proximal engaging element may be configured to be removed during the operation. For instance, as illustrated in FIGS. 13-15, the distal tip of the proximal engaging element is connected to a connector directly (e.g. FIGS. 14 and 15) or indirectly (e.g. via a connecting wire as illustrated in FIG. 13). With these configurations, the distal tip of the proximal engaging element would be moved away from the body lumen via movement of the connector. More particularly, when the proximal connector of the distal element together with a clot moves proximally, it may pull the distal tip of the proximal engaging element proximally and fold the proximal element into the desired basket shape with the tip being round shape, or atraumatic. Therefore, the risk of damaging the body lumen by directly contacting the body lumen surface (e.g. blood vessel) would be substantially reduced, in at least some embodiments. These tip features also makes it possible for the proximal engaging element to be pushed forward in the lumen when needed and not injure the surface of the lumen.

In some embodiments, the proximal engaging element is configured to significantly improve clot engagement and retrieval efficiency. For example, as demonstrated in FIG. 3, an occlusion may be disposed between the proximal and distal engaging elements when using the device according to some embodiments. This design has an improved ability to engage an occlusion or clot more firmly by holding it with two separate engaging elements.

The proximal engaging element can be made of metal materials. Some non-limiting examples of such metal materials for the proximal engaging element include nickel-titanium (NiTi) alloy, stainless steel, titanium and its alloys, and cobalt chrome (CoCr) alloys. Alternatively, any polymers or plastics which have desired properties for a proximal engaging element can be used. In some embodiments, the proximal engaging element is made of flexible material (s). In further alternative examples, the proximal engaging element can be constructed using two or more different materials, e.g. as illustrated in FIG. 15.

In some embodiments, a diameter of the proximal engaging element may vary from approximately 1 to 8 mm at its expanded state. In certain embodiments, the diameter of the proximal engaging element at its expanded state may be approximately 1 mm, 2 mm, 3 mm, 4 mm, 5 mm, 6 mm, 7 mm, and 8 mm or any range therebetween. In some other embodiments, a length of the proximal engaging element may vary from approximately 2 to 40 mm. In certain embodiments, the length of the proximal engaging element may be approximately 2 mm, 5 mm, 7 mm, 10 mm, 12 mm, 15 mm, 17 mm, 20 mm, 22 mm, 25 mm, 27 mm, 30 mm, 32 mm 35 mm, 37 mm, 40 mm or any range therebetween. Further, in alternative embodiments, the length of the proximal engaging element may be more than 40 mm.

The proximal engaging elements are in general flexible and with elastic or super-elastic properties. Thus the proximal engaging element may be varied in its shape. The proximal engaging element, typically comprise at least two different configurations which are referred to a "collapsed (i.e. folded or closed)" configuration, and a "relaxed (i.e. unfolded or open)" configuration. The collapsed configuration of the proximal engaging element generally represents a status in which the outer radius of the proximal engaging element becomes minimized. When the proximal engaging element is in a microcatheter, the proximal engaging element is in its collapsed configuration. When the proximal engaging element is out of microcatheter and is unconstrained, the proximal engaging element is in its relaxed status. In some embodiments, the proximal engaging element is made of elastic or super-elastic material, and thus is self-expandable. Due to its flexible property, the proximal engaging element may be easily placed into the microcatheter by gently pulling or pushing the same toward the microcatheter. In further alternative embodiments, the proximal engaging element may have more than two different statuses. For example, as demonstrated in FIGS. 13-15, the proximal engaging element may be configured to change its shape during the operation, and resultantly there would many different statuses between the complete collapsed and the complete relaxed statuses.

In some embodiments, one or more markers may be added to the device. Such markers may include radiopaque materials which help monitor the position and or movement of the device in the body. Some non-limiting examples of radiopaque markers may comprise gold, gold alloys, CoCr alloy, platinum, or platinum alloys. Marker(s) can also be in form of radiopaque coating. The markers may be added anywhere in the device. In some embodiments, one or more markers may be added at the distal engaging element so that a location of the distal engaging element in the body would be determined. In some other embodiments, one or more markers may be added at the proximal engaging element so that a location of the proximal engaging element in the body would be determined. In still some other embodiments, both of the distal and proximal engaging elements contain markers. The markers in each of the distal and proximal engaging elements may be the same or different materials. Alternatively, one or more markers may be added to the central wire and/or the tubing compartment. In some embodiments, the markers may be approximately 0.10 to 4 mm long, and the diameter is approximately 0.001 to 0.030 inch. However, any variations in any dimensions (e.g. length, diameter, size, and mass) and in shapes of markers are suitable.

In some embodiments, the device may comprise tubing compartments. Tubing compartments may comprise a plurality of tubing elements. Such tubing elements may include a pusher tubing and a connecting tubing. The pusher tubing may further comprise an inner pusher tubing, a middle pusher tubing, an outer pusher tubing in at least some embodiments. Also in alternative embodiments, the pusher tubing may comprise a distal pusher tubing and a proximal pusher tubing. Various materials can be used to manufacture the tubing elements, which may include metal and non-metal materials. In some embodiments, the distal pusher tubing and/or an outer pusher tubing can be made from lubricious and flexible polymers such as PTFE or PET. The middle and proximal pusher tubing can be made from Nitinol super-elastic material, stainless steels, CoCr alloys, titanium alloys, or polymers (such as Polyimide, PEEK, etc.). One or more of the tubing elements can also be coated with lubricious material, such as PTFE coating, hydrophilic coating etc. The tubing elements can also be made of composite materials, such as PTFE or FEP (Fluorinated ethylene propylene) tubing over Nitinol wire, or PTFE or FEP tubing over Stainless Steel etc.

The central wire can be in the form of a wire, braid, or tubing. Some non-limiting examples of metal materials for the central wire may comprise nickel, titanium, stainless steel, cobalt, chrome and any alloys of the foregoing such as Nitinol (NiTi), or Cobalt Chromium alloys. In addition, any polymers or plastics which have desired properties of being the central wire can be used for production of the same. Polymers include, but not limited to, Polyimide, PEEK (Polyether ether ketone), Nylon, PTFE (polytetrafluoroethylene), PET (Polyethylene terephthalate), Polypropylene, etc. Polymer coated metal including but not limited to, PTFE coated Stainless Steel, or PTFE coated NiTi can also be used as a central wire. Also a hydrophilic coating can be applied.

In some embodiments, the diameter of the pusher tubing and the connecting tubing may be approximately 0.001 to 0.050 inch. In other embodiments, the diameter of the pusher tubing and the connecting tubing may be smaller than 0.001 inch or over 0.050 inch. In still some other embodiments, the device may comprise a pusher tubing, but not a connecting tubing.

For the purpose of illustration, some non-limiting and illustrative examples of the device according to the invention are provided in the following figures. While only few exemplary applications are described herein for the purpose of illustration, many different modifications and alternations, which should be obvious to a person with ordinary skill in the art, can also be done without affecting the scope of the invention. Therefore, not only the examples disclosed in this application but also such obvious modifications and alterations should also be included in the scope of the invention.

FIG. 1 illustrates a device according to one aspect of the invention. The device may comprise a tubing component and an engaging compartment. The tubing component may comprise a plurality of tubing elements such as a pusher tubing 20 and connecting tubing 30. The engaging compartment may comprise a distal engaging element 90 and a proximal engaging element 60. The device may further comprise a central wire 10.

As seen in FIG. 1, in certain embodiments, the distal engaging element 90 and the proximal engaging element 60 are associated with the central wire 10. In certain some embodiments, the distal engaging element 90 may be connected (or fixed) to the central wire 10, and the proximal engaging element 60 may be connected to the connecting tubing 30, which is also connected to the pusher tubing 20. The central wire 10 may be placed inside the connecting tubing 30 and the pusher tubing 20, and move freely through the connecting tubing as well as the pusher tubing. In some embodiments, the central wire 10 and the pusher tubing 20 may extend to the proximal end of the device.

In some embodiments, the central wire 10 and the connecting tubing 30 may be maneuvered independently, thereby allowing separate control of the distal and the proximal engaging elements. More particularly, the distal engaging element would be controlled by movement of the central wire which is connected to the distal engaging element; and the proximal engaging element would be controlled by movement of the connecting tubing, or pusher tubing, which is connected to the proximal engaging element. In certain embodiments such as those seen in FIG. 1, the pusher tubing and the connecting tubing are connected to each other, and thus movement of the pusher tubing may ultimately control the proximal engaging element.

In certain embodiments, the distal engaging element may have an open-end at its distal end (e.g. see FIG. 1A). Alternatively, in certain other embodiments, the distal element may have a closed-end at its distal end (e.g. see FIG. 1C). The distal engaging element 90 may be connected to the central wire 10. The distal engaging element may be connected at about its proximal end to the central wire by various means, e.g. welding, gluing or clipping.

In certain embodiments, the connection between the central wire 10 and the distal engaging element 90 is placed in the distal element connector 80. The distal element connector may be in form of a short tube or coil and placed over the central wire 10. In some embodiments, the distal element connector may comprise an outer distal element connector 82 and/or a distal element joining media 81. In such embodiments, the proximal end of the distal engaging element may be placed in between the outer connect and central wire. On some occasions, the distal engaging element, connector and the central wire may be connected by joining media such as a clip, clasp or fastener which fastens or holds the distal engaging element and the central wire together.

According to some embodiments, the proximal engaging element may comprise a plurality of wires. Alternatively, the proximal engaging element may be made from a tubing, e.g. by a laser cutting technique. Therefore, in certain embodiments, a small segment of the tubing is saved at the proximal end and the struts are cut or formed at the distal end as seen in FIG. 1A'. In such embodiments, the tubing segment at the proximal end that is an integral part of the proximal engaging element may serve as a proximal element connector. In alternative embodiments, a separate proximal element connector may be added to the device as seen in FIG. 1A. In some embodiments, the proximal element connector 40 may comprise a plurality of elements, such as joining media 41 and an outer proximal element connector 42. In such embodiments, the proximal end of the proximal engaging element may be placed at the inner proximal element connector, at the outer proximal element connect or between the outer proximal element connectors and the tip of the connecting tubing. In some embodiments, the proximal end of the proximal engaging element is placed in the inner proximal element connector. In some occasions, the proximal end of the proximal engaging element and the connector may be jointed using media such as a clip, clasp or fastener which fastens or holds the proximal engaging element, more particularly the proximal end of the proximal engaging element. Alternatively, the proximal element connector may comprise a single layered tubing in which the proximal engaging compartment is placed.

When a separate proximal element connector is present (e.g. FIG. 1), the connection of the proximal engaging element to the proximal connector can be done via various means, such as welding or gluing. Alternatively, as discussed above, the proximal connector may comprise a joining media which can fasten or hold the proximal engaging element. In any event the proximal element connector surrounds the central wire and allows the free movement of the central wire inside the proximal element connector.

In certain some embodiments, the device contains a connecting tubing which is connected to the proximal engaging element. In some embodiments, the connecting tubing may be further connected to the pusher tubing, e.g. as illustrated in FIG. 1. With this configuration, the proximal engaging element is permanently connected to the pusher tubing. However, alternatively, fixation of the proximal engaging element to the pusher tubing is temporal or reversible, and thus the proximal engaging element, optionally along with the proximal connector, can be dissociated from the pusher tubing if desired. As a further alternative, the proximal engaging element and the proximal element connector associated thereto may not be fixed at the tubing compartment (see, e.g. FIG. 7). Instead, they can freely slide along the central wire.

According to one aspect of the invention, the position of the distal engaging element can be determined by controlling the central wire. For example, in the embodiment illustrated in FIG. 1, the distal engaging element is connected with the central wire. An operator is able to control the movement of the central wire (e.g. pushing in and out) to locate the distal engaging element in a desired position. In certain embodiments, the proximal engaging element may be positioned via movement of the tubing element, e.g. a pusher tubing, a connecting tubing or both. As illustrated in FIG. 1, in some embodiments, the proximal engaging element is fixed at about the distal end of the tubing element(s). Accordingly, an operator can locate the proximal engaging element in a desired position by controlling the tubing element, i.e. a pusher tubing and connection tubing. With these configurations, the two engaging elements can be maneuvered independently. Further, it allows that the distance between the two engaging elements can be varied. This aspect of the device where the distance between the two engaging elements is variable is beneficial when treating patients with the device. This design has the ability to engage an occlusion or clot firmly by holding it between the two separate engaging elements. Further, by adjusting the position of each engaging element, and the distance therebetween, it can maximize the efficiency and accuracy of the holding.

Figure 1B:
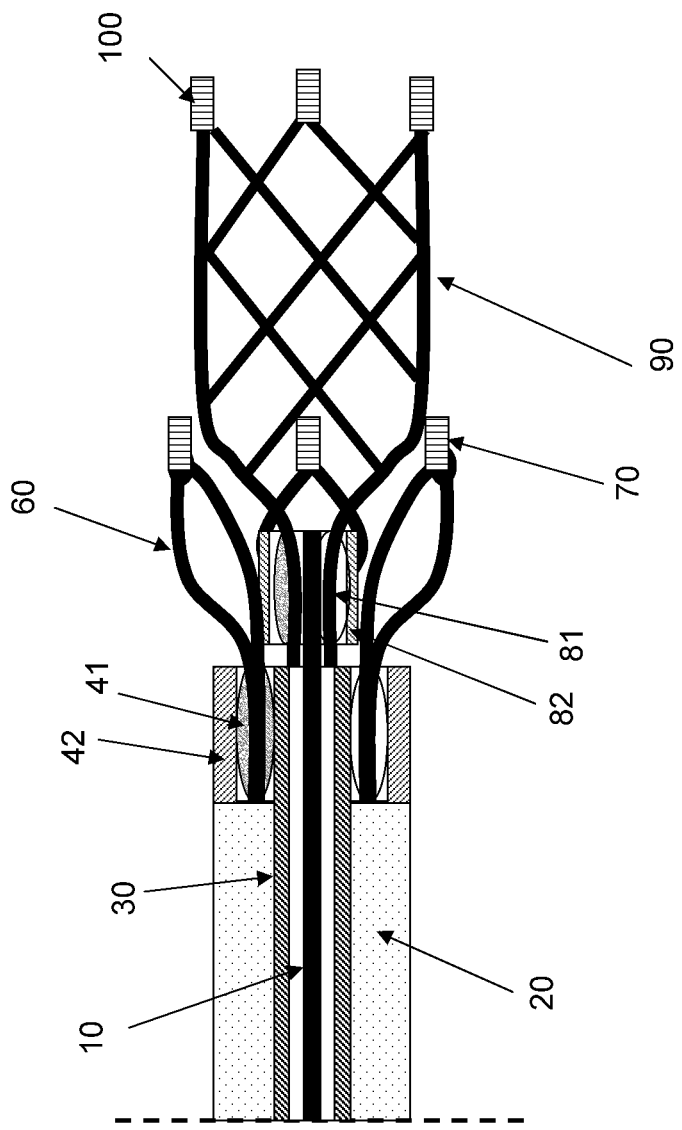
FIG. 1B shows a closed status of the device (between the distal and proximal engaging elements) and FIG. 1C shows a device with closed ended distal tip of the distal engaging element.
Figure 1C:
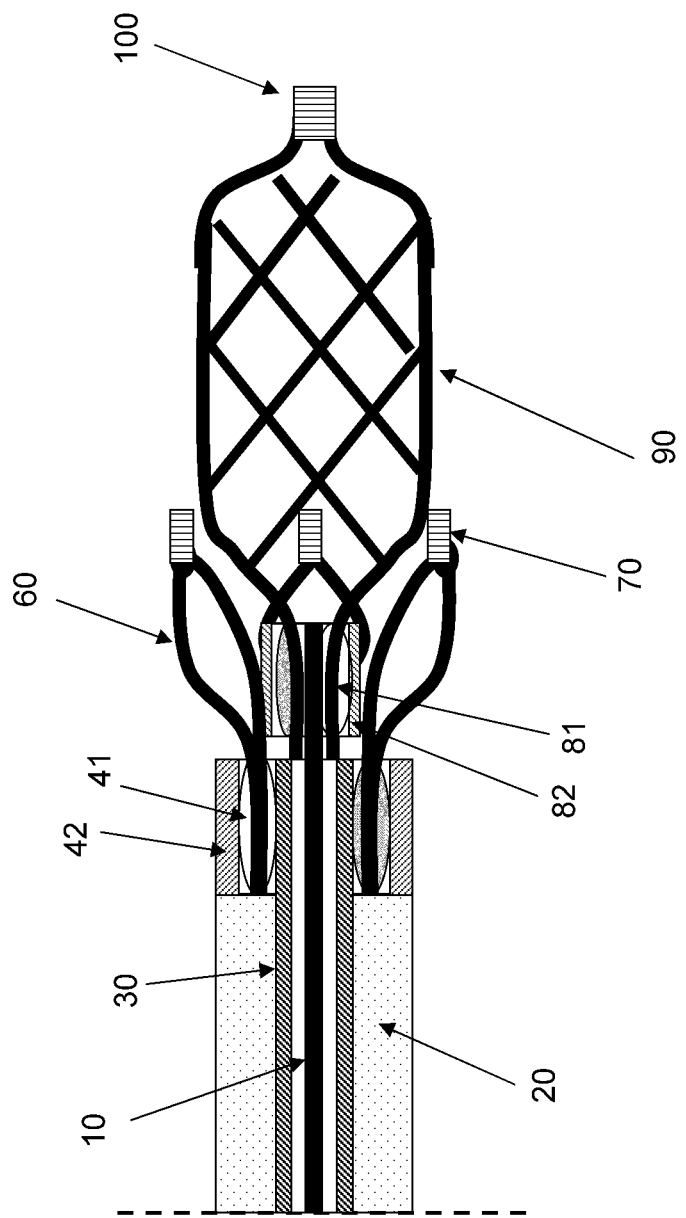

In FIG. 1B, a different status of the device illustrated in FIG. 1A is illustrated. In this closed position, the central wire is pulled proximally and thus the distal engaging element is pulled toward the proximal engaging element, shortening the distance between the two engaging elements.

FIG. 2 shows an illustrative embodiment of removing a clot or occlusion from a body lumen (e.g. blood vessel). In certain embodiments, the device may be used to engage a clot or occlusion and remove the same from the body lumen as follows:

(A) A microcatheter 5, with guidance of a guide wire is first disposed to an area where an occlusion occurs in a body lumen. Depending on hardness, length, location, and shape of the clot or occlusion, the microcatheter may partially penetrate the clot (or occlusion), or pass distal to the clot. Following this, the tubing compartment and the engaging components may be delivered to the occlusion through the microcatheter. In this technique, the proximal expendable element is separated from the distal expendable element. When placing the device, the tip of the proximal engaging element is placed behind/proximal to the clot or occlusion (B) The microcatheter pulled back to unsheath the engaging components and part of the tubing compartment. Ideally, the proximal engaging element is proximal to the clot, and the distal engaging element is distal to the clot, or distal to the proximal portion of the clot, if the clot is substantially long. In some embodiments, the clot would be held or engaged at least in part by the distal engaging element at this stage as seen in the FIG. 2B.

(C) An operator can further adjust the position(s) of one or both of the engaging elements if desired. For example, while holding the pusher tubing to fix the proximal engaging element, the operator can proximally pull the central wire that is connected to the distal engaging element. Then the clot would be moved proximally due to the friction between the distal engaging element and the clot. As this occurs, the distance between the two engaging elements is shortened, and the clot is grabbed or engaged in and/or between the two engaging elements. If the operator feels the resistance while pulling the central wire and the distal engaging element, this may indicate that the clot is engaged in and/or between the two engaging elements. He or she can then lock the positions of the distal and proximal engaging elements and pull the device and the engaged clot, together with the microcatheter, from the body lumen (e.g. an artery). In some embodiments, the location of the device can be identified by markers 70 and/or 100 placed on the device.

Figure 3:
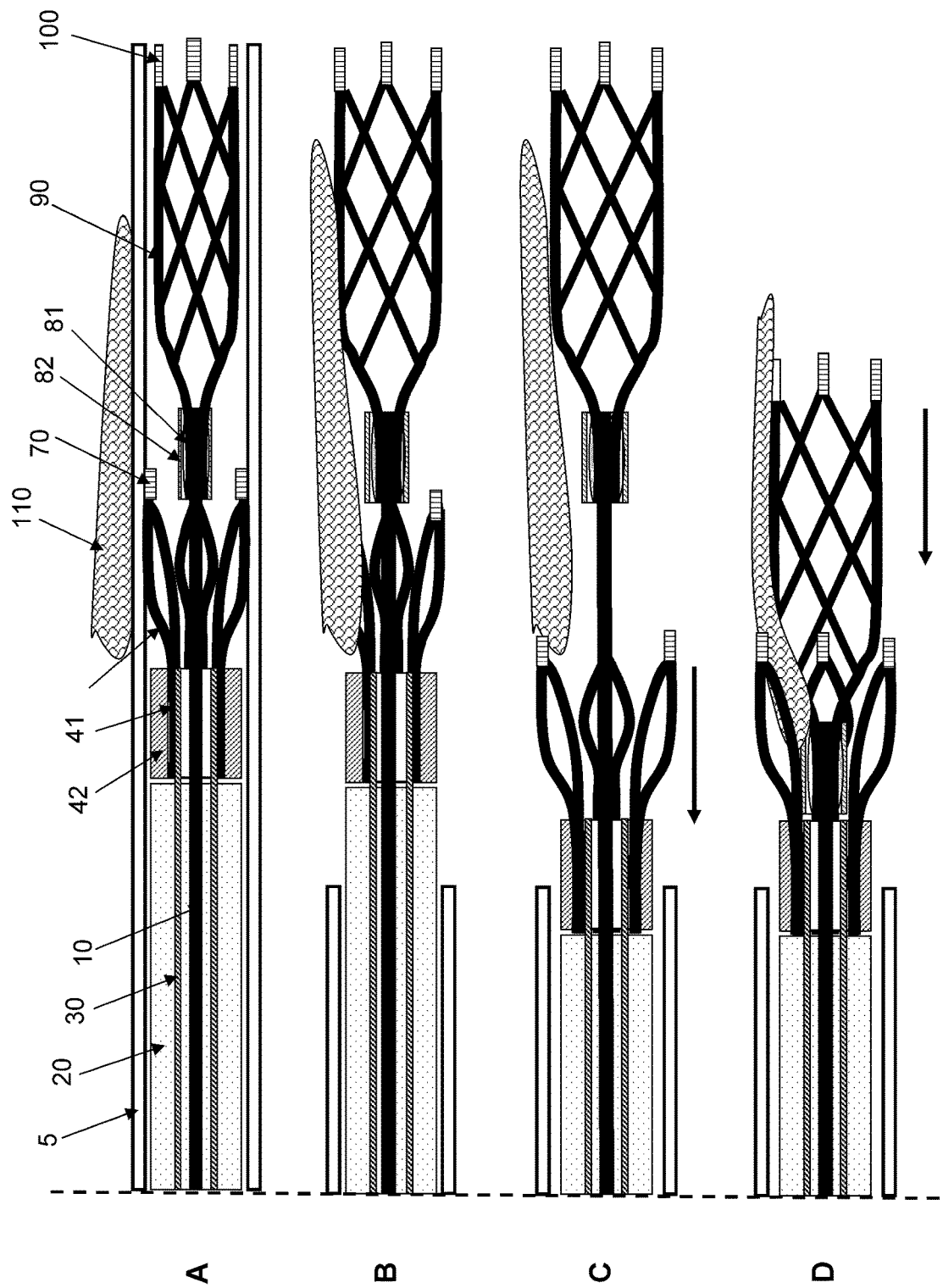
FIG. 3 shows another non-limiting illustrative embodiment of a method for removing an occlusion or part of an occlusion from a body lumen according to the invention.

In FIG. 3, an alternative embodiment or technique of removing a clot or occlusion from a body lumen is illustrated. The device may be used to engage a clot or occlusion and remove the same from the body lumen as follows:

(A) A microcatheter 5 is navigated to an area where an occlusion occurs in a body lumen. The microcatheter may be advanced over the distal end of the clot or occlusion. Depending on hardness, size, location and shape of the clot or occlusion, the microcatheter may penetrate the clot (or occlusion), or pass by the clot without substantially disturbing the clot. In some embodiments, the tubing compartment and the engaging compartment are introduced into the microcatheter once the microcatheter is in position near the occlusion area. In certain occasions, an operator may dispose the microcatheter and the expendable compartment in a position such that once unsheathed the proximal engaging element is distal to the proximal end of the clot. As explained elsewhere in the application, the location of the device can be monitored, for example, by using the markers present in the device.

(B) The microcatheter is unsheathed, and the engaging compartment and part of the tubing compartment are exposed.

(C) The operator can further adjust the position(s) of one or both of the engaging elements. For example, while holding the central wire and consequently the distal engaging element stable, pulling the proximal engaging element back until its distal end just passes the proximal end of the clot. This can be indicated by viewing the markers 70 in the distal end of the proximal engaging element. The distal end of the proximal engaging element is open at this position. Alternatively, if desired, the distal engaging element can be adjusted while the proximal engaging element is on hold. Further, if desired, the proximal and distal engaging elements may be adjusted together to ensure the engagement of the clot.

(D) While keeping the proximal engaging element stable by fixing the pusher tubing, an operator can pull the central wire that is connected to the distal engaging element. Then the clot may be moved proximally due to the friction between the distal engaging element and the clot. The distance between the two engaging elements is shortened, and the clot is grabbed or engaged in and/or between the two engaging elements. If the operator feels the resistance while pulling the central wire and the distal engaging element, it may indicate that the clot is engaged in and/or between the two components. He or she can then lock the positions of the distal and proximal engaging elements and pull the device and the engaged clot, together with the microcatheter, from the body lumen (e.g. an artery). In some embodiments, the location of the device and microcatheter can all be identified by markers 70 and/or 100 placed on the device.

Some advantages of the embodiment illustrated in FIG. 3 include that the proximal engaging element can be positioned proximal to the clot after unsheathing, to ensure relatively high precision in the placement of the engaging component with respect of the clot or occlusion. Because the proximal engaging element can be put immediately behind the clot or occlusion, when pulling the distal engaging element to move the clot proximally, the clot only needs to travel for a very short distance before it is engaged between the two engaging elements. Thus the chance of the clot being lost is reduced as compared to the technique shown in FIG. 2.

Figure 4:
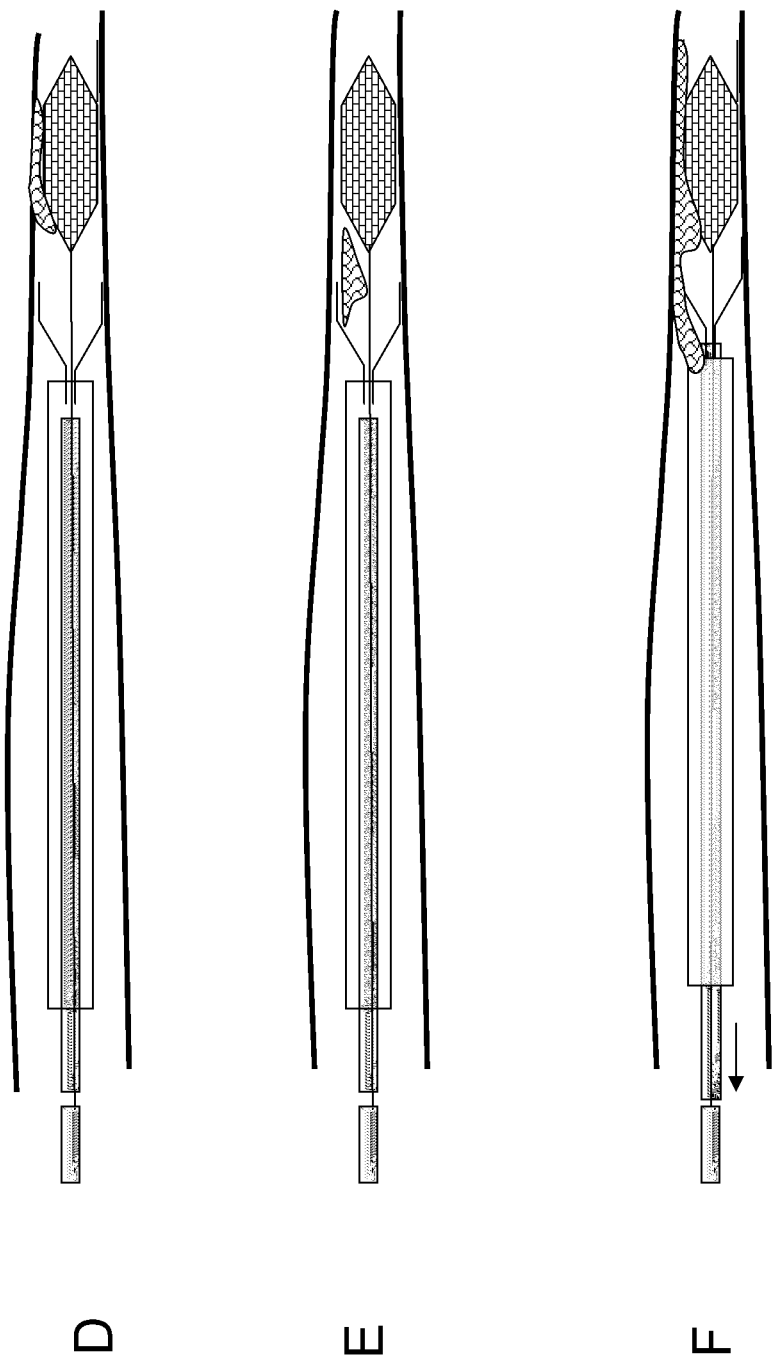
FIG. 4 shows some other non-limiting illustrative embodiments of a method for removing an occlusion from a body lumen according to the invention.

In FIG. 4, some additional mechanisms of engaging the clot using the device are presented. As depicted in FIG. 4, the clot may engaged between the tubing element and the body lumen surface (e.g. an artery wall) (4A), between the microcatheter and the proximal engaging element (FIG. 4B), between the proximal engaging element and the artery wall (4C), between distal engaging element and artery wall (4D), between the proximal and distal engaging elements (4E), and between proximal engaging element and the microcatheter tip and at the same time between the two engaging elements (4F). Therefore, it would be apparent that various modifications and applications of the device and method disclosed in the present application would be possible without departing the scope and spirit of the invention. Accordingly, any of such variations and modifications is of course encompassed by the scope of the invention.

FIG. 5 illustrates an illustrative embodiment of a system comprising the foregoing device. In some embodiments, the central wire 10 can extend to the proximal end of the device, and be jointed to a distal component handle 120. The length of the system from its distal end to proximal end may be approximately 100 to 200 cm. In some embodiments, the length of the system from its distal end to proximal end may be approximately 100 cm, 110 cm, 120 cm, 130 cm, 140 cm, 150 cm, 160 cm, 170 cm, 180 cm, 190 cm, and 200 cm. In some other embodiments, the length of the system from its distal end to proximal end may be shorter than 100 cm or longer than 200 cm. In some embodiments, the system may comprise a plurality of pusher tubing such as a proximal pusher tubing 24, a middle pusher tubing 22, and a distal pusher tubing 25. In some other embodiments, the connecting tubing may be connected to the middle and proximal pusher tubings. Both the distal and proximal engaging elements can be operated at the distal end of the system, i.e. with the distal component control handle and the proximal pusher tubing as illustrated in FIG. 5, by an operator.

FIG. 6 illustrates an alternative embodiment of a system in which a distal pusher tubing and a proximal pusher tubing are present. On top of the connection tubing, there is a distal pusher tubing. In some embodiments, at least some part of the distal pusher tubing is flexible to ensure the device being able to navigate through tortuous path. In other embodiments, at least some part of the distal pusher tubing may be lubricious and flexible, and thus it also enhances pushability of the device. In certain embodiments, the proximal end of the pusher tubing can be made from a stiff/firm tubing to enhance the device pushability.

In case the device needs to be pulled back into the microcatheter, each of the engaging elements can be operated separately. For example, the proximal engaging element can be first pulled back into the microcatheter, and then the distal component can be pulled into the microcatheter by pulling the central wire avoiding the two elements (and their struts) being overlapped. This will avoid the two expendable elements overlapping each other and not being able to be pulled into the microcatheter. In certain embodiments, the positions of the two engaging elements may be locked once the clot is engaged. In such embodiments, movement of the two engaging elements would be synchronized and their introduction into the microcatheter would be in succession.

Figure 7B:
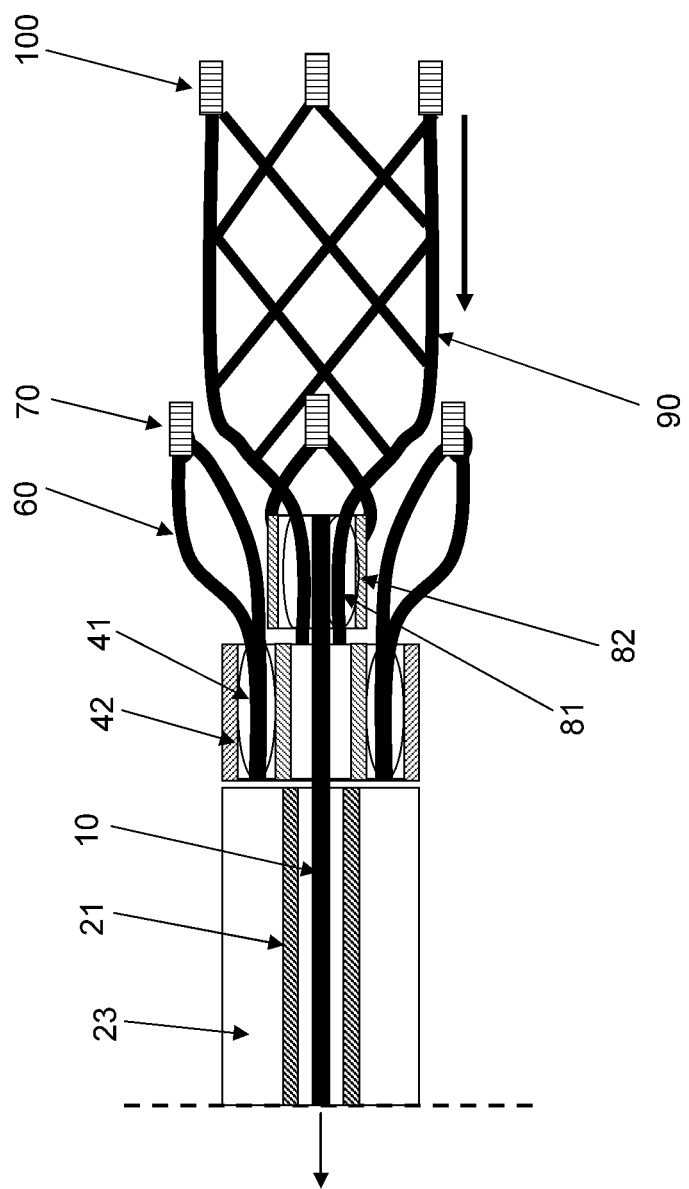

FIG. 7 illustrates an alternative embodiment of the device. In particular, the proximal engaging element may not be connected with the tubing compartment. Rather, the proximal engaging element 60 that is associated with the proximal element connector 40 may freely slide along the central wire 10 as seen in FIG. 7A. In some embodiments, the inner diameter of the proximal element connector 40 is lager than the outer diameter of the central wire 10, and thus the proximal engaging element 60 that is associated with the proximal element connector 40 can slide freely on the central wire 10. Further, a connecting tubing may not be in need in at least some embodiments. FIG. 7B shows a closed-status of the embodiment shown in FIG. 7A where the central wire 10 is pulled proximally and thus the distal engaging element 90 moves toward the proximal engaging element 60. This will shorten the space (or distance) between the two engaging elements. This feature would enable the device to engage a clot as illustrated in the next figure.

Figure 8:
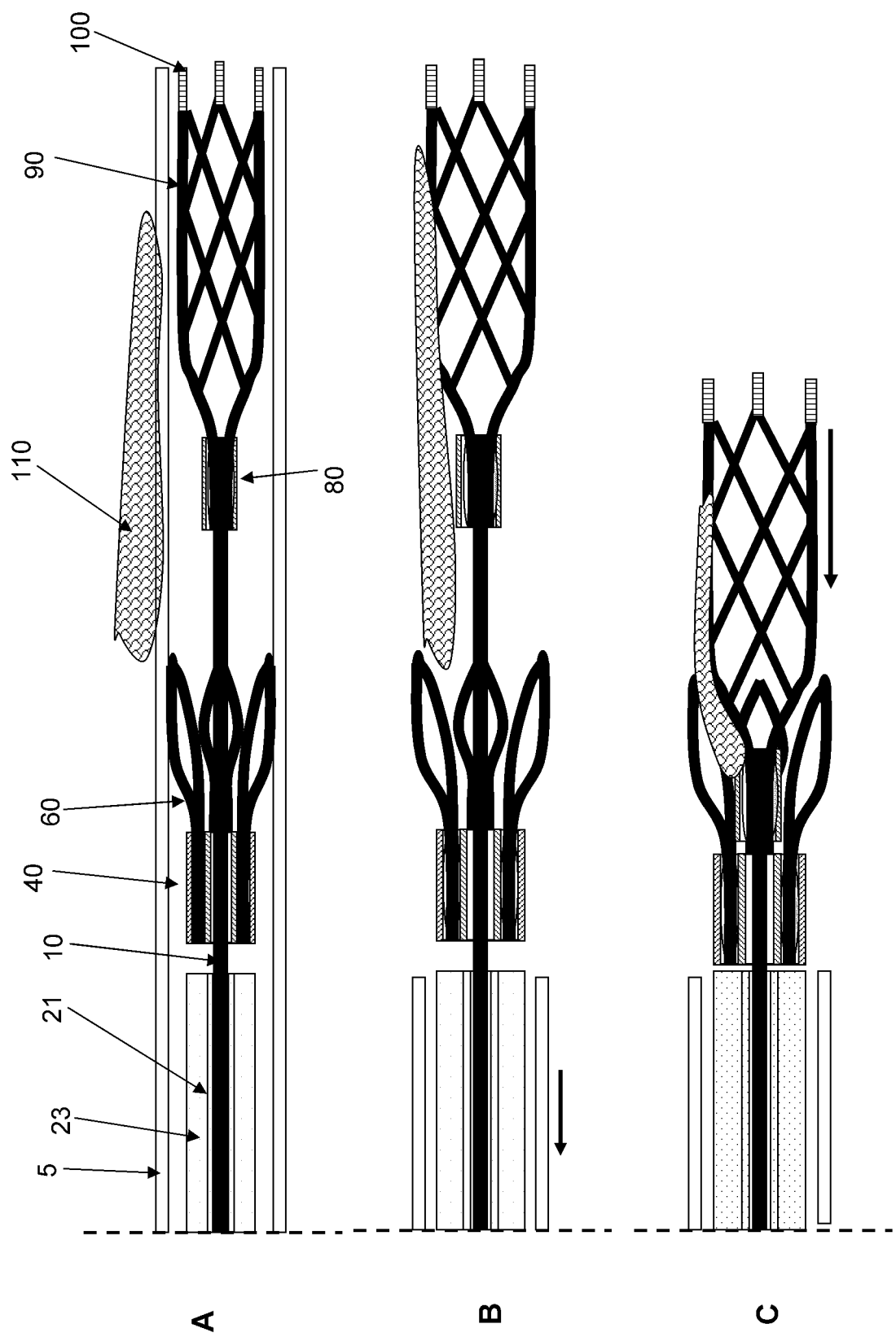
FIG. 8 shows a non-limiting illustrative embodiment of a method for removing an occlusion or part of an occlusion from a body lumen according to the invention.

FIG. 8 shows an illustrative embodiment of removing a clot or occlusion from a body lumen (e.g. blood vessel), especially using the device shown in FIG. 7. In certain embodiments, the device may be used to engage a clot or occlusion and remove the same from the body lumen as follows:

(A) A microcatheter 5, with guidance of a guide wire is first navigated to an area where an occlusion occurs in a body lumen. The microcatheter may be positioned distal to the proximal end of the clot or occlusion. Depending on hardness, size, location and shape of the clot or occlusion, the microcatheter may penetrate the clot (or occlusion), or pass by the clot without substantially disturbing the clot. Then the tubing compartment and the engaging compartment may be delivered to the occlusion through the microcatheter. The proximal expendable element is separated from the distal expendable element. When placing the device, the tip of the proximal engaging element is placed proximal to the clot or occlusion.

(B) The microcatheter is unsheathed, and the engaging compartment and part of the tubing compartment are exposed. An operator can adjust the device so that the proximal engaging element may be proximal to the clot, and the distal engaging element may be distal to the clot, or at least passing part of the clot, if the clot is substantially long. In some embodiments, the clot would be held at least in part by the distal engaging element at this stage as seen in the figure.

(C) An operator can further adjust the position of the distal engaging elements. For example, the operator can proximally pull the central wire that is connected to the distal engaging element. Then the clot would be moved proximally due to the friction between the distal engaging element and the clot. The distance between the two engaging elements is shortened. When the clot contacts the proximal engaging element, the clot can be grabbed or engaged in and/or between the two engaging elements. In the meantime, the engaging compartment and the clot is future pulled to near the microcatheter tip. To ensure the engagement, the operator may lock the position of the distal engaging element and pull the device.

In certain embodiments, the process illustrated in FIG. 8 can be performed as follows: while performing the process demonstrated in FIG. 7, there may be friction between the microcatheter lumen and the proximal engaging element when the device is unsheathed, and the proximal engaging element is pulled away from the distal engaging element. The distance between the two engaging elements may be maximized or substantially extended once the two elements are out of the microcatheter. An operator may not need to adjust the positions of the two engaging elements after deployment. An operator can pull the distal engaging element proximally through the pusher tubing which is connected to the central wire. Therefore, the distance between the two components will be shortened to engage the clot. In certain occasions, the tip of microcatheter may be used to prevent the proximal engaging element moving backward. When the operator feels resistance while pulling the pusher tubing/central wire proximally, it may indicate that the clot is engaged in and/or between the two engaging elements and the proximal engaging element is also stopped by the tip of microcatheter. At this point the device can be locked and removed from the body lumen. Therefore the clot or occlusion can be removed easily and with high efficiency.

Figure 9:
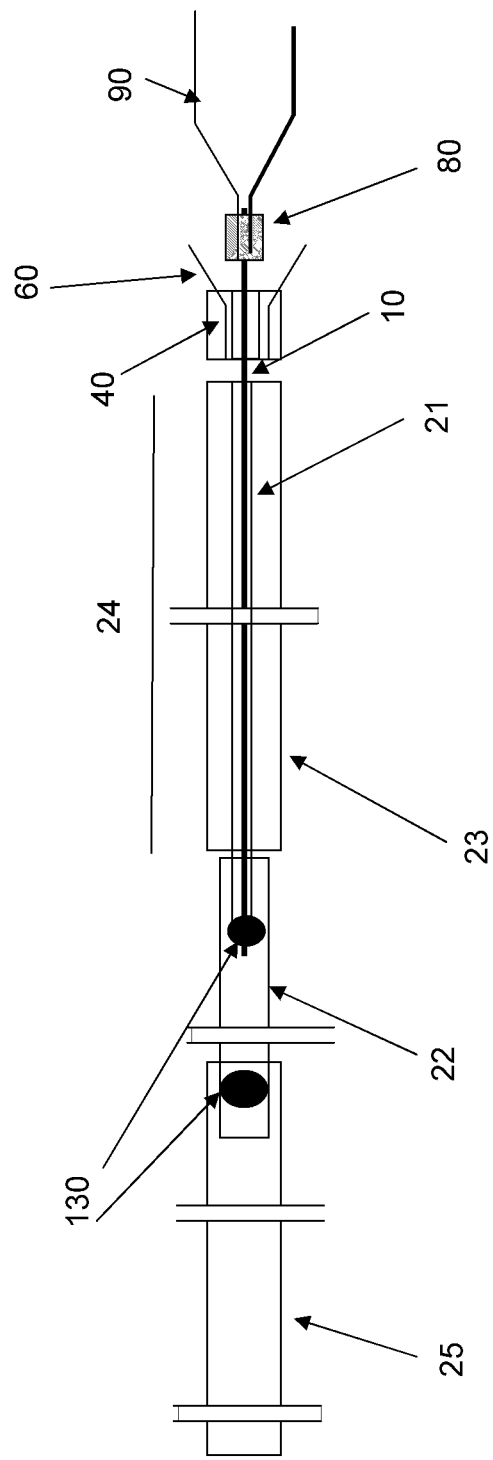
FIG. 9 shows a still another non-limiting illustrative embodiment of a system according to the invention.

FIG. 9 illustrates another illustrative embodiment of a system comprising the device illustrated in FIG. 7. Alternatively, the device illustrated in FIG. 1 can be used in this system of FIG. 9. In some embodiments, the proximal engaging element 60 is around the central wire 10, and thus it can slide freely between the distal engaging element 90 and the distal tip of the pusher tubing 140. In addition, the distal engaging element 90 may be connected to the central wire 10. The central wire 10 can extend to the proximally. The central wire 10 may be joined with at least one of the pusher tubings (e.g. proximal pusher tubing 24, middle pusher tubing 22, inner pusher tubing 21, and outer pusher tubing 23). Therefore, unlike the embodiment illustrated in FIG. 5, the central wire 10 does not necessarily extend to the proximal end of the device. Instead, it may be connected with any of the tubing elements, and be controlled along with the connected tubing. In some embodiments, the outer pusher tubing 23 may be flexible and lubricious, and placed close to the distal end of the system so that it may allow the device to pass through tortuous path in the lumen. Further, in some other embodiments, a thin inner pusher tubing 21 may be present in the system, and this inner pusher tubing 21 may be flexible yet can increase the pushability of the system. In still some other embodiments, a middle pusher tubing 22 with certain flexibility may be present in the system. In still some other embodiments, a proximal pusher tubing 24 that is relatively stiff may be present in the system so that the pushability of the system may be further improved. One or more pusher tubings can be connected with adhesives to each other, and also with other parts including a central wire 10. In still some other embodiments, a single pusher tubing with variable stiffness can be used in this device to replace multiple pusher tubings and junctions. This tubing can be made by grinding the tubing into different wall thicknesses, or through spiral cutting to ensure the distal end being more flexible and proximal end being more stiff.

Figure 10:
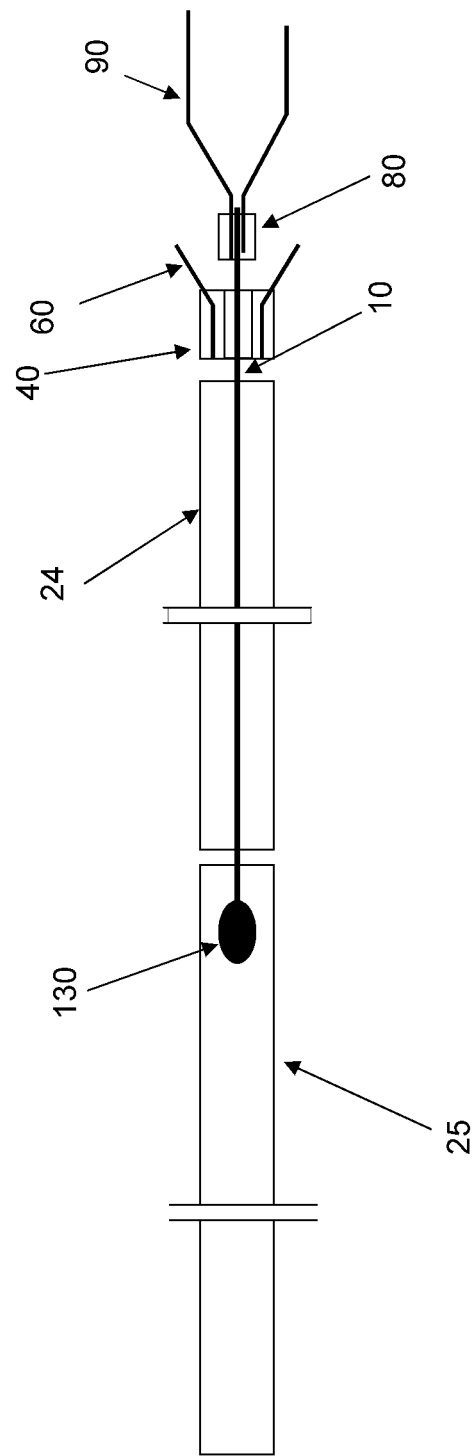
FIG. 10 shows a still another non-limiting illustrative embodiment of a system according to the invention.

FIG. 10 illustrates an alternative embodiment of a system in which a distal pusher tubing and a proximal pusher tubing are present. In this embodiment, the central wire 10 may not extend to the proximal end of the system. Similar to the example shown in FIG. 9, the central wire is connected to one or more of the tubing elements, and controlled via the connected tubing elements. On top of the connection tubing, there is a distal pusher tubing. In some embodiments, at least some part of the distal pusher tubing is flexible to ensure the device being able to navigate through tortuous path. In other embodiments, at least some part of the distal pusher tubing may be lubricious and flexible, and thus it also enhances pushability of the devise. In certain embodiments, the proximal end of the pusher tubing can be made from a stiff/firm tubing to enhance the device pushability.

Figure 11A:
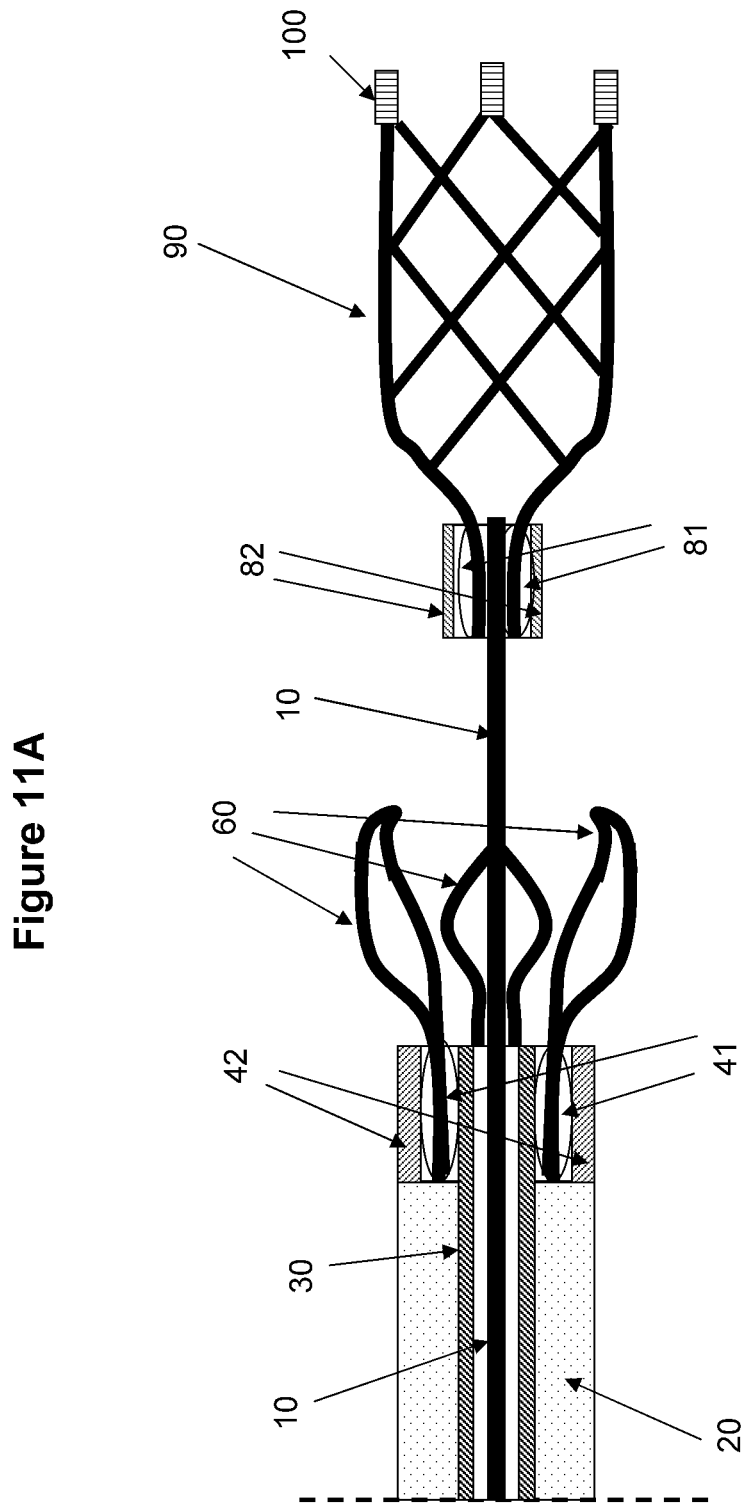
FIG. 11A shows an open status of the device and FIG. 11B shows a closed status of the device.
Figure 11B:
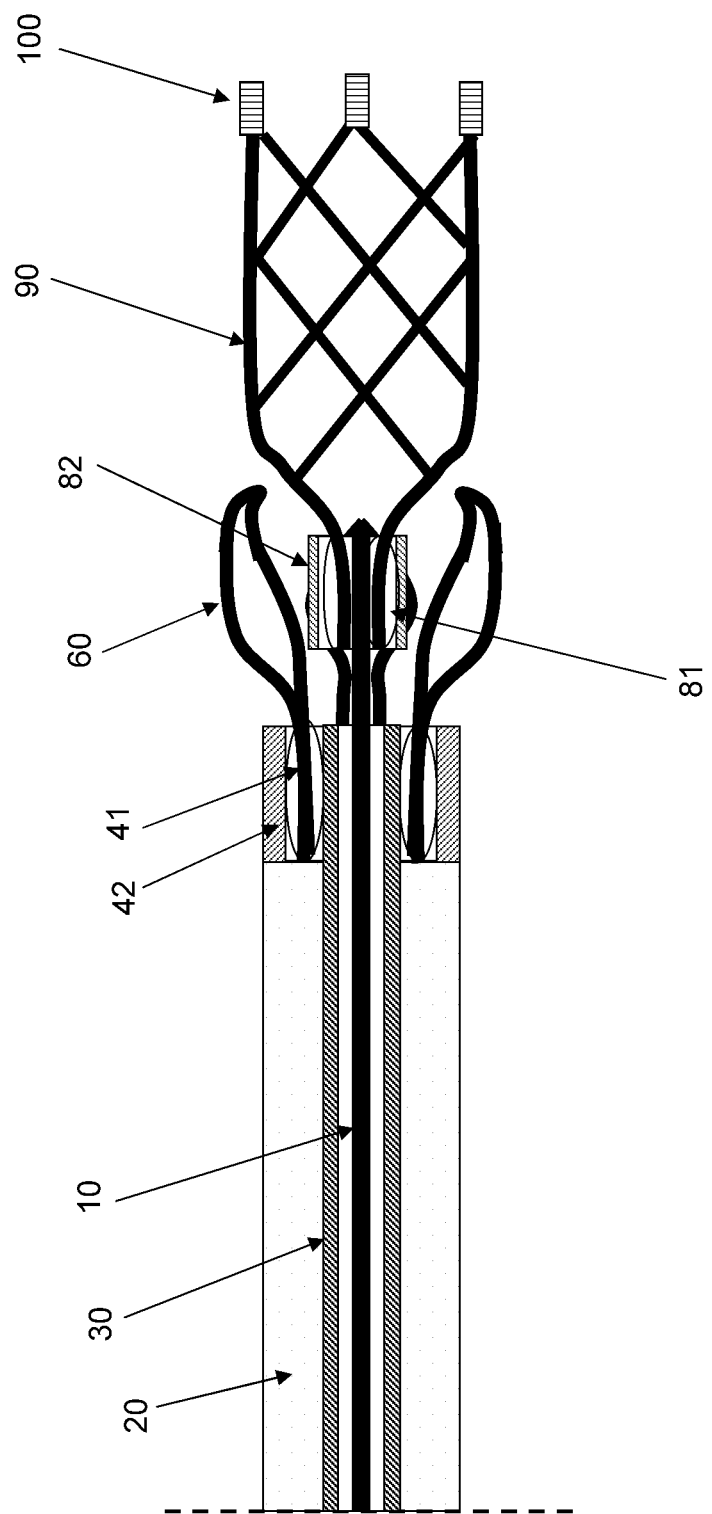

FIG. 11A illustrates an alternative embodiment of a device. Unlike the embodiment illustrated in FIG. 1, this device comprises a push-able and pull-able proximal engaging element. In this design, however, the distal tip of the proximal engaging element is modified. The distal end of the proximal engaging element may be bent inward or smoothed as shown in FIG. 11 which may further ensure that the tips are atraumatic to the inner wall of the artery. Thus it can be pulled and pushed in the artery lumen with much lower risk of damaging the artery wall. FIG. 11B illustrates a closed-status of the device shown in FIG. 11A where the distance between the proximal and distal engaging elements is minimized.

Figure 12:
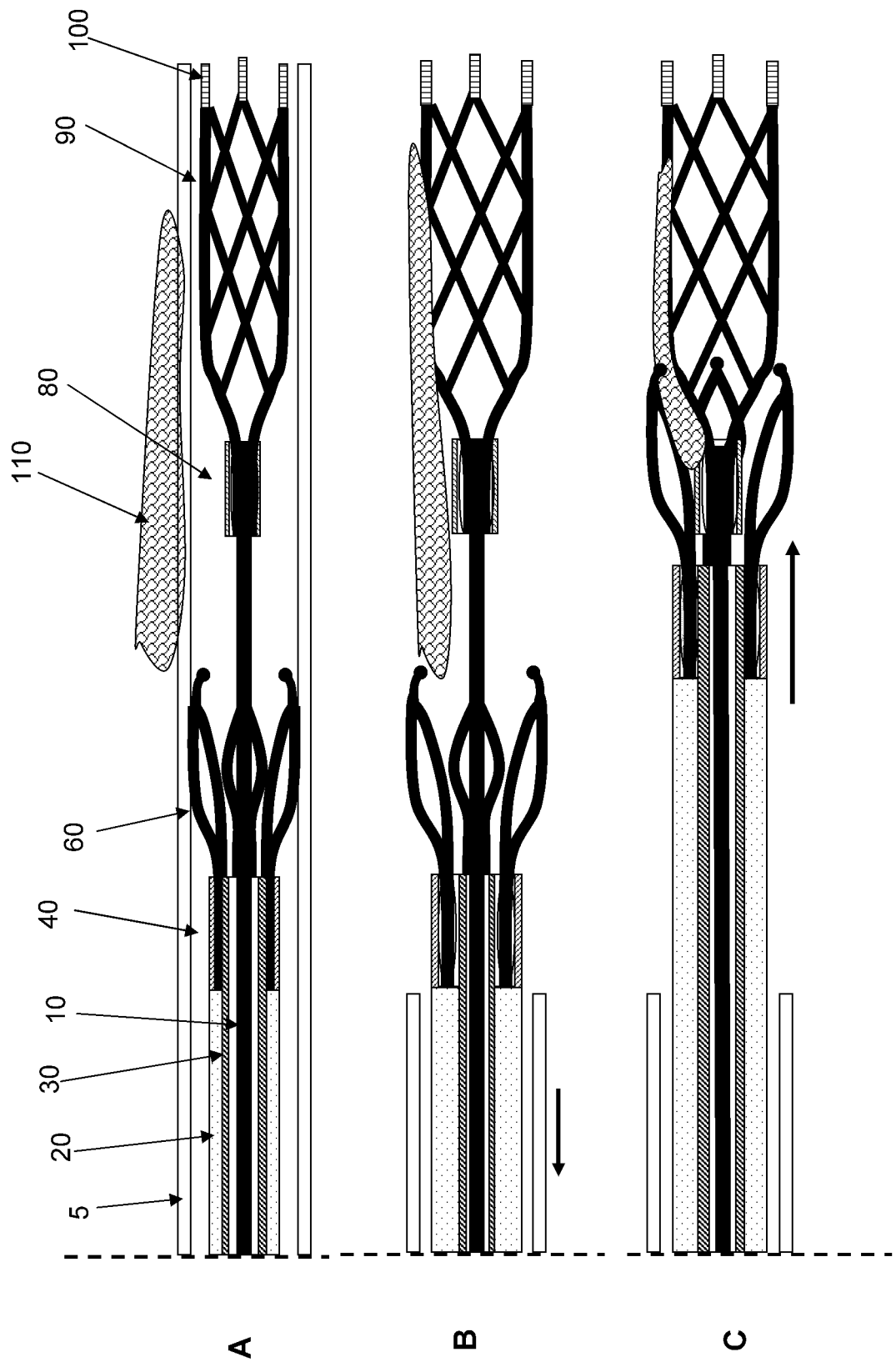
FIG. 12 shows a still another non-limiting illustrative embodiment of a method for removing an occlusion from a body lumen according to the invention.

FIG. 12 shows an illustrative embodiment of removing a clot or occlusion from a body lumen (e.g. blood vessel), especially using the device illustrated in FIG. 11. The clot retrieval mechanism illustrated in this figure is largely similar to that in FIGS. 2 and 3.

The device according to some embodiments of the present invention has significant advantages. For example, during the operation if the clot is not in and/or between the two engaging elements, or one or both the engaging elements is either too distal or too proximal to the clot, an operator can position one or both of the engaging elements to ensure the engagement. Especially, in the embodiments illustrated in FIG. 12, the proximal engaging element is adjusted to a desired position by pulling or pushing through the connection tubing. Because the proximal element has an atraumatic round tip and can be pushed forward to engage the clot with the distal element, the procedure/technique may avoid the need to pull the clot for a distance with distal engaging element only, which may further reduce the possibility of losing the clot during the procedure. Therefore, such a device can engage with the clot using the two engaging elements, and stabilize the same until the clot is removed from the body lumen. This independent control of the two engaging elements allow very fine adjustment of the device during the procedure, and therefore it is highly useful, especially in settings when precise positioning in treatment is necessary (e.g. stroke treatment in brain).

Figure 13A:
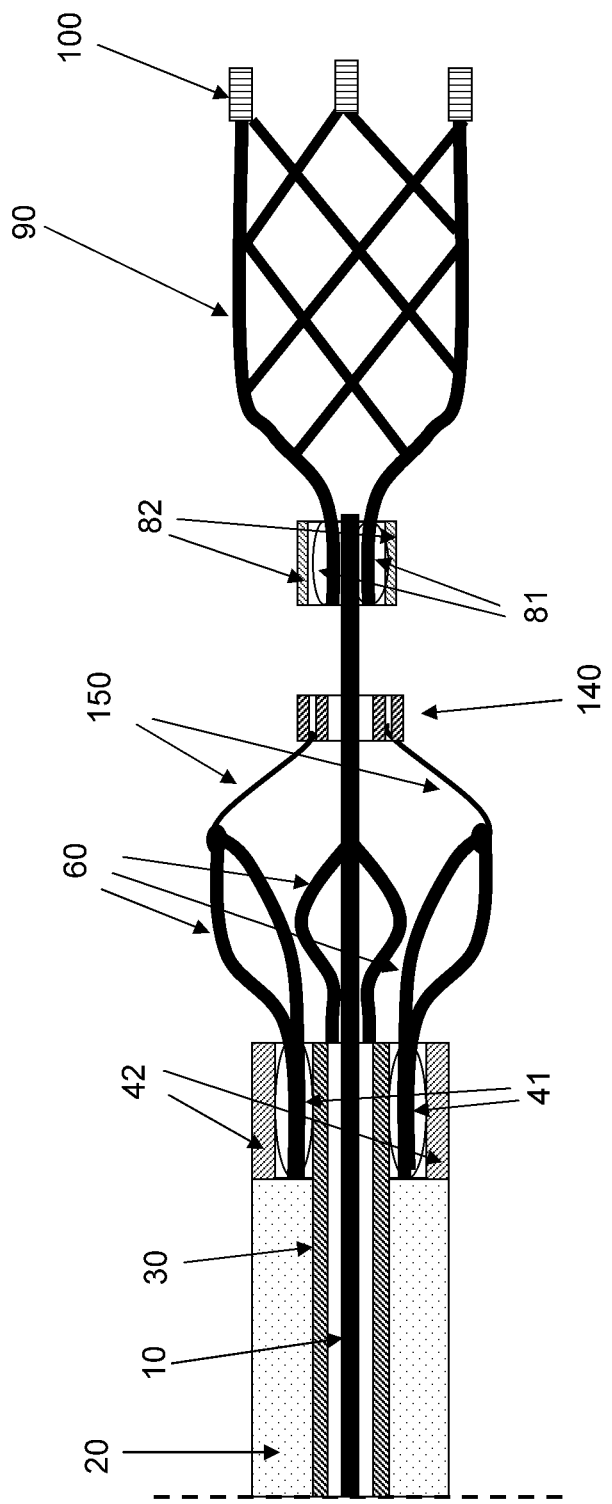
FIG. 13A shows an open status of the device and FIG. 13B shows a closed status of the device where an occlusion is engaged with the device.
Figure 13B:
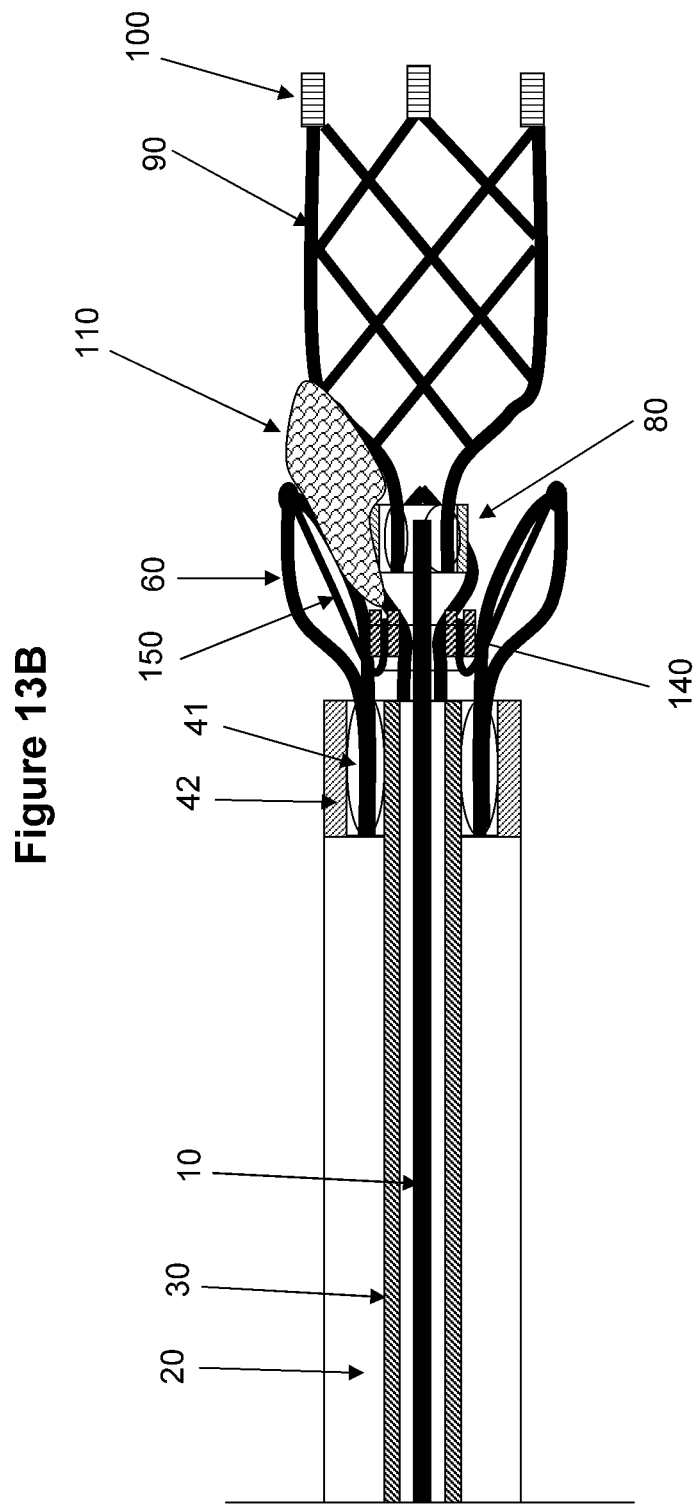

FIG. 13A illustrates an alternative embodiment of a device. In this particular embodiment, the proximal engaging element has a basket-like feature. There is no relatively sharp end on this proximal engaging element 60 because the distal ends of the proximal engaging element are connected to a distal connector 140 of the proximal engaging element via a connecting wire 150 of proximal engaging element. Therefore, when the proximal engaging element is compressed, the distal end thereof will move backward and form a smooth distal end as shown in FIG. 13B. This smooth ends is atraumatic to the artery inner lumen. This proximal engaging element is pull-able and push-able in body lumen in at least some embodiments. In certain embodiments, the distal end of the proximal engaging element is thinner than the other part thereof. Thus, when a clot is pulled or pushed in and/or between the two engaging elements, the distal portion of the proximal engaging element may buckle, or invert as seen in FIG. 13B so that engagement of the clot by the proximal engaging element would not be hindered by additional association between the proximal engaging element 60 and the distal connector of proximal element 140.

Figure 14A:
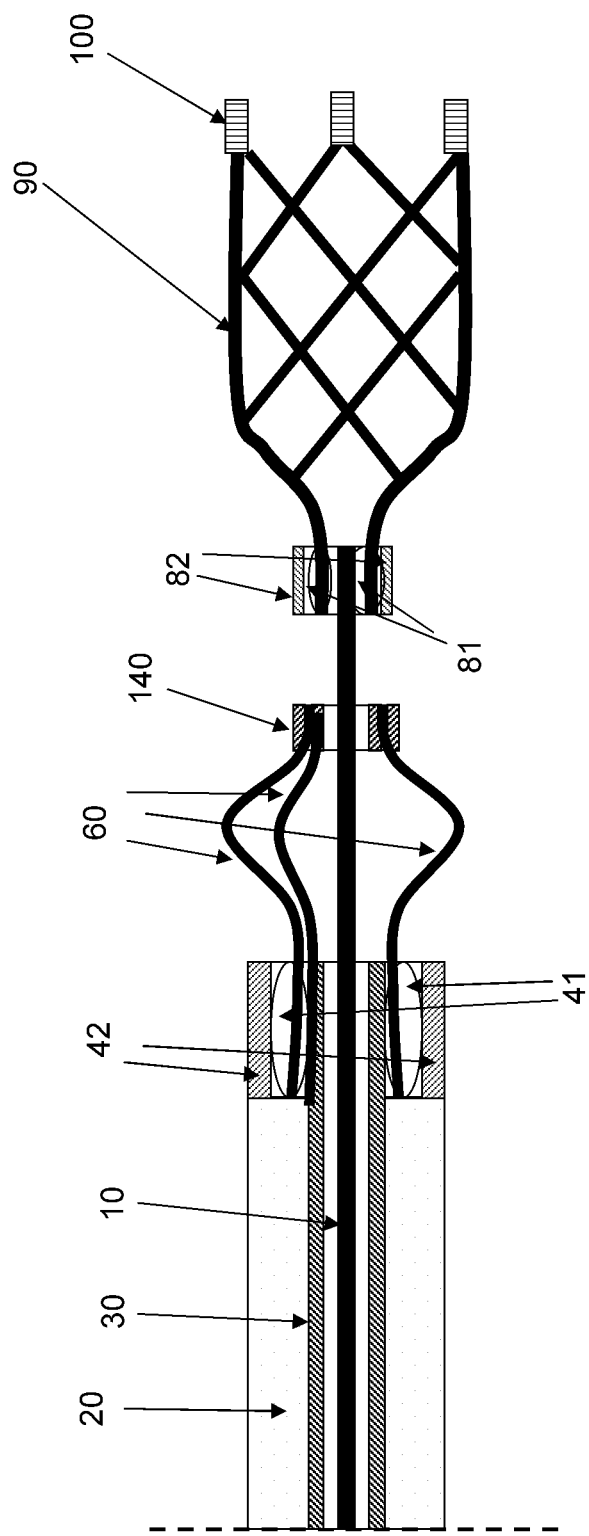

FIG. 14A illustrates a further alternative embodiment of a device. In this particular embodiment, the proximal engaging element has a basket-like feature. However, unlike the embodiment illustrated in FIG. 13, the distal end of the proximal engaging element 60 is directly jointed with the distal connector of proximal component 140. This device also has no sharp end on the proximal engaging element, and thus further reduces any risks damaging the body lumen. In this design, the material used in a proximal portion of the proximal engaging element could either be same as, or different from, the other portion thereof. In certain embodiments, the distal portion of the proximal engaging element may be made of a relatively flexible element than the other portion thereof. Accordingly, when a clot is pulled against the proximal engaging element, the distal portion of the proximal engaging element may be buckle or invert so that the proximal engaging element can better engage with the clot as seen in FIG. 14B.

Figure 15A:
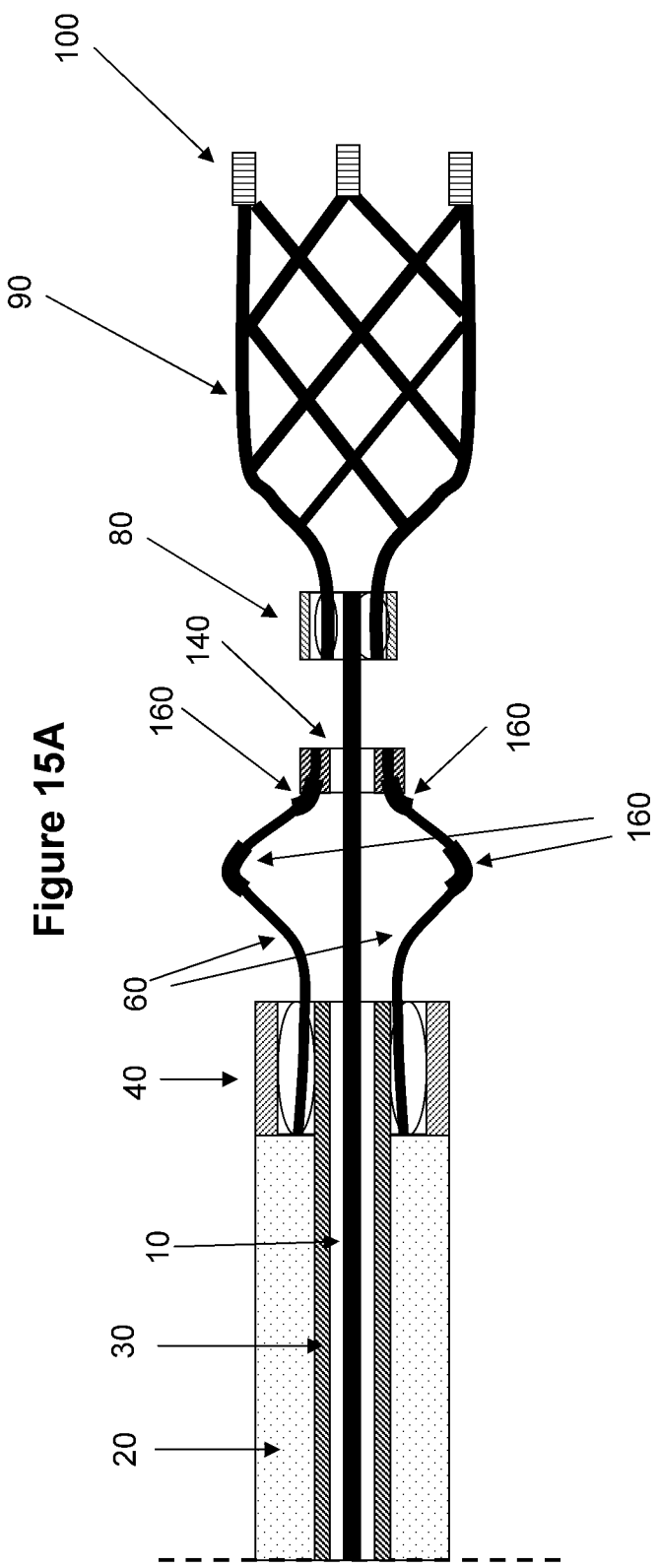

FIG. 15A illustrates a further alternative embodiment of a device. This device also comprises additional features for further ensuring the safety of the device. This design may comprise the proximal engaging element having a basket like feature. The distal portion of the proximal element is jointed to the proximal portion of the proximal element through soft/flexible connectors (e.g. a segment connect 160) which allow buckling while the distal portion if compressed backward. This proximal engaging element is pull-able and push-able, e.g. by controlling the tubing compartment associated with the proximal engaging element. There is no sharp end in the proximal engaging element, and therefore it is atraumatic to the artery wall. Moreover, in this design, the proximal engaging element may be made of more than one material, one of which is softer than the other. Therefore, it is easy to buckle or invert at least the distal portion of the proximal engaging element when engaging with the clot (see FIG. 15B).

FIG. 16 illustrates a further alternative embodiment of the proximal portion a device. This device also comprises additional features for further ensuring the safety of the device. This design comprises the proximal engaging element with round distal ends to make the tips more atraumatic to the vessel. Thus the proximal engaging element is pull-able and push-able, e.g. by controlling the tubing compartment associated with the proximal engaging element.

The following FIGS. 17-26 provide further alternative embodiments where a proximal element for engaging (and removing) a clot is located at the distal tip or end of a microcatheter. In some embodiments, this engaging element may be attached at the distal tip of the microcatheter. In some other embodiments, a distal tip or end of a microcatheter itself is shaped and configured to act as a proximal engaging element. In other words, the proximal engaging element is an integral part of the microcatheter.

In some embodiments, a proximal engaging element, which may be separately attached to or an integral part of the microcatheter, can change a shape and/or size during a retrieval process or when needed. For instance, after a retrieval device is placed in the desired position, i.e. fully or partially passing a clot, the retrieval device may be inserted to a microcatheter. The microcatheter can then be pulled proximally to unsheathe the device. When the distal tip of the microcatheter reaches at about the proximal end of the clot, the distal tip of the microcatheter is maneuvered to change into an open/funnel shape. While holding the microcatheter stable, the retriever device can be pulled back with the clot that may be partially engaged with the engaging element of the retriever until the clot is substantially or fully engaged (or captured) between the distal tip of the microcatheter (i.e. the proximal engaging element) and the engaging element of the retriever (i.e. the distal engaging element). By locking the retrieval device and the microcatheter at the proximal end of the devices, the device and the microcatheter together with the engaged clot can be pulled out from the lumen, e.g. an artery In certain embodiments where the microcatheter distal tip provides a proximal engaging element, it may simplify a design of a retrieval device, and consequently the manufacturing process thereof. Instead of two separate engaging elements, e.g. as illustrated in an embodiment of FIG. 1, the retrieval device may need only one engaging element, i.e. a distal engaging element, as another element acting as a proximal engaging element can be provided from the microcatheter.

FIG. 17 illustrates an embodiment of a device where an inflatable or engaging element such as a balloon is attached at the distal end/tip of the microcatheter. The shape and size of the inflatable or engaging element 170 may be controlled by its inflation and deflation. According to some embodiments, the inflatable or engaging element 170 can be inflated e.g. by injecting a liquid 195 (e.g. a saline solution) with a syringe 190 into the inflatable or expandable 170 element so as to form a desired shape. The injected liquid can be transferred to the inflatable or expandable element 170 through an injection channel 180 in certain some embodiments. The shape and size of the inflatable or engaging element 170 after being inflated can be varied. For instance, when a preformed balloon is attached at the distal tip of the microcatheter, it can be shaped into any preformed shape, e.g. a funnel-like form, when inflated, as seen in FIG. 17B. Alternatively, merely the surface area of the inflatable or engaging element 170 can be increased upon inflation as seen in FIG. 17C. This transformable proximal engaging element provided by the microcatheter can engage the clot alone or in combination with other elements (e.g. a surface of the body lumen, the microcatheter, the tubing compartment, the proximal engaging element, the distal engaging element, and any combinations thereof) with high efficiency (see, e.g. FIGS. 4 and 18).

Figure 18:
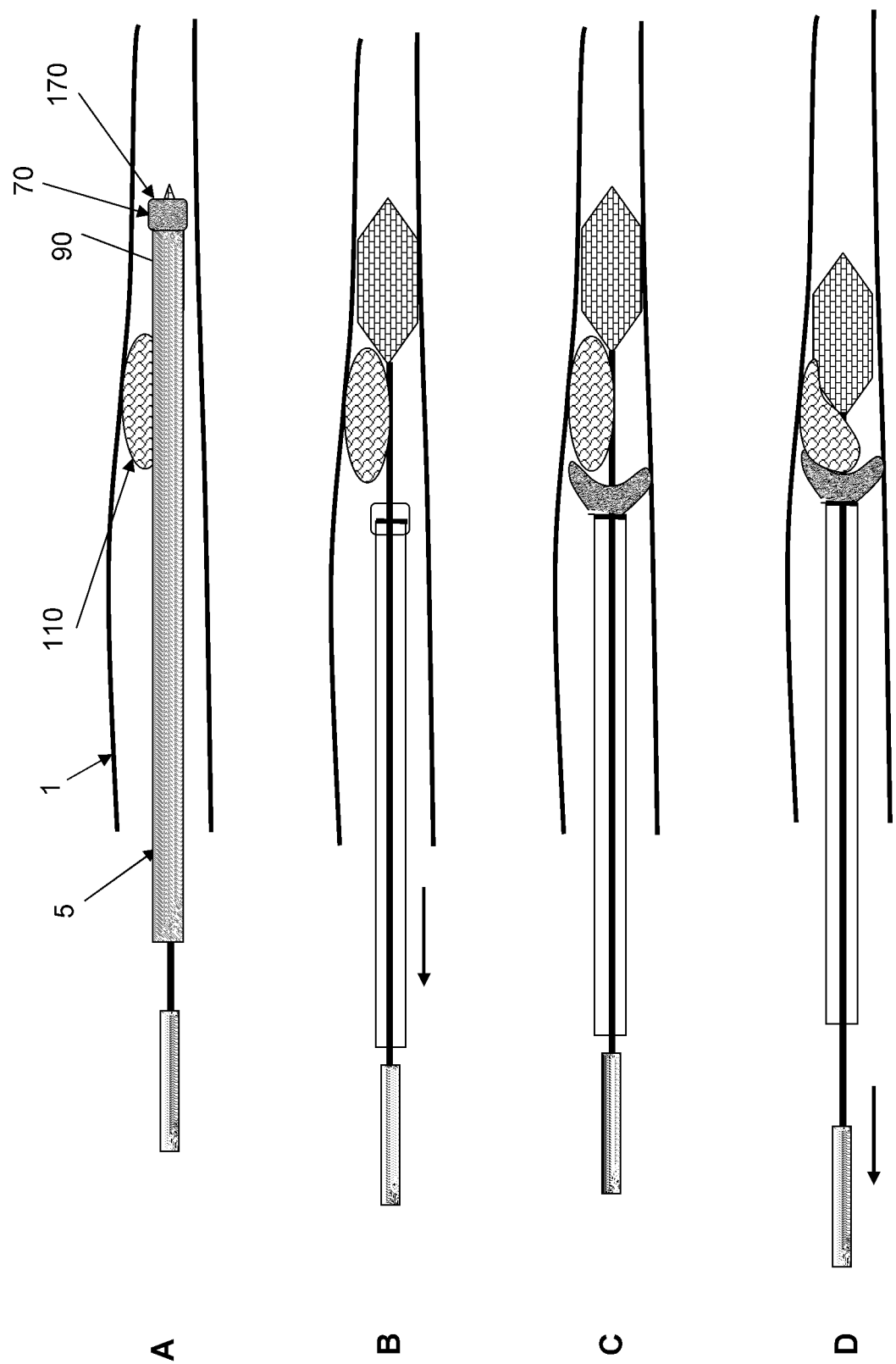
FIG. 18 shows a non-limiting illustrative embodiment of a method for removing an occlusion from a body lumen according to the invention, especially using a device illustrated in FIG. 17.

FIG. 18 shows a mechanism to engage and remove a clot using the device of FIG. 17. During the retrieval procedure, an operator may insert the microcatheter 5 into a body lumen (e.g. an artery) until the distal tip passes into or through the clot 110. The retrieval device may be delivered to the occlusion position along with the microcatheter, or through the microcatheter once the microcatheter is at the position. In certain embodiments, the retrieval device may be pushed until its engaging element 90 may pass at least portion of the clot as seen in FIG. 18A. While holding the retrieval device stable, the operator may pull the microcatheter backward (i.e. proximally) until the microcatheter's distal tip is at about the proximal end of the clot, and the engaging element 90 of the retrieval device is exposed, and expanded to its relaxed or open state (FIG. 18B). Therefore, the clot may be located between the distal engaging element 90 and the distal tip of the microcatheter (i.e. the proximal engaging element 170). Then, the operator may expand the transformable distal tip of the microcatheter 170 to transform the tip into a funnel shape at the proximal end of the clot (FIG. 18C). While holding the microcatheter stable, the operator may pull the distal engaging element 90 back so that the clot may be moved backward and engaged between the distal engaging element 90 and the distal tip of the microcatheter 170. The operator then can fix the microcatheter and the retrieval device and pulling them out of the artery which results in the removal of the clot.

Figure 19:
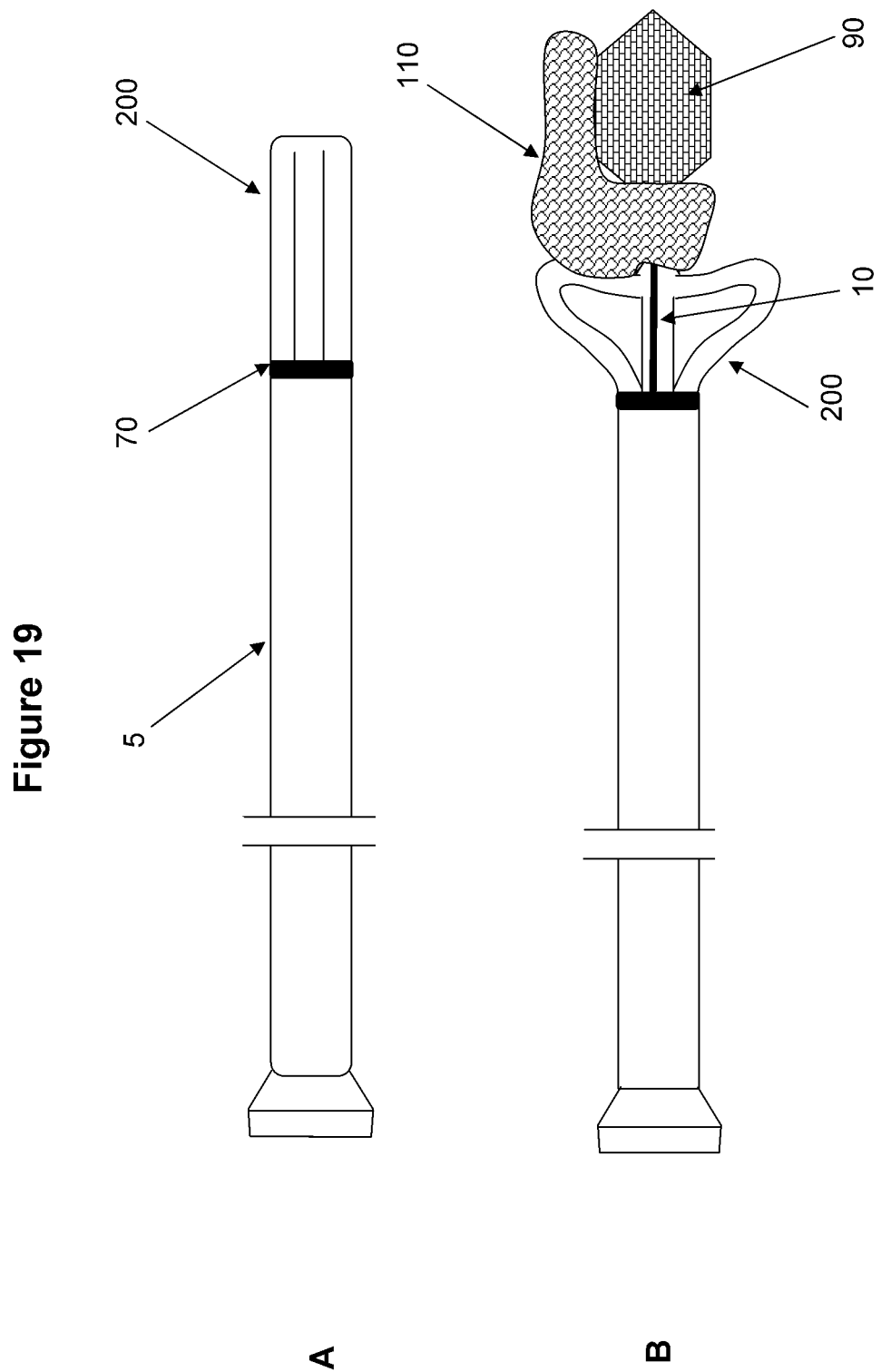
FIG. 19 shows another non-limiting illustrative embodiment of a device according to the invention where a microcatheter comprises a transformable tip at about its distal end.

FIG. 19 illustrates another embodiment of a device where a distal tip of a microcatheter forms an engaging element, more particularly a proximal engaging element. In this particular embodiment, a distal tip of the microcatheter 200 is cut, e.g. by a laser cutting, so that it can transform into a funnel shape when compressed by the clot 110 and/or the distal engaging element 90 during a retrieval procedure (FIG. 19B). In certain embodiments, the cutting process ends before reaching the very end of the microcatheter distal tip so that the very distal tip of the microcatheter is still closed.

Figure 20:
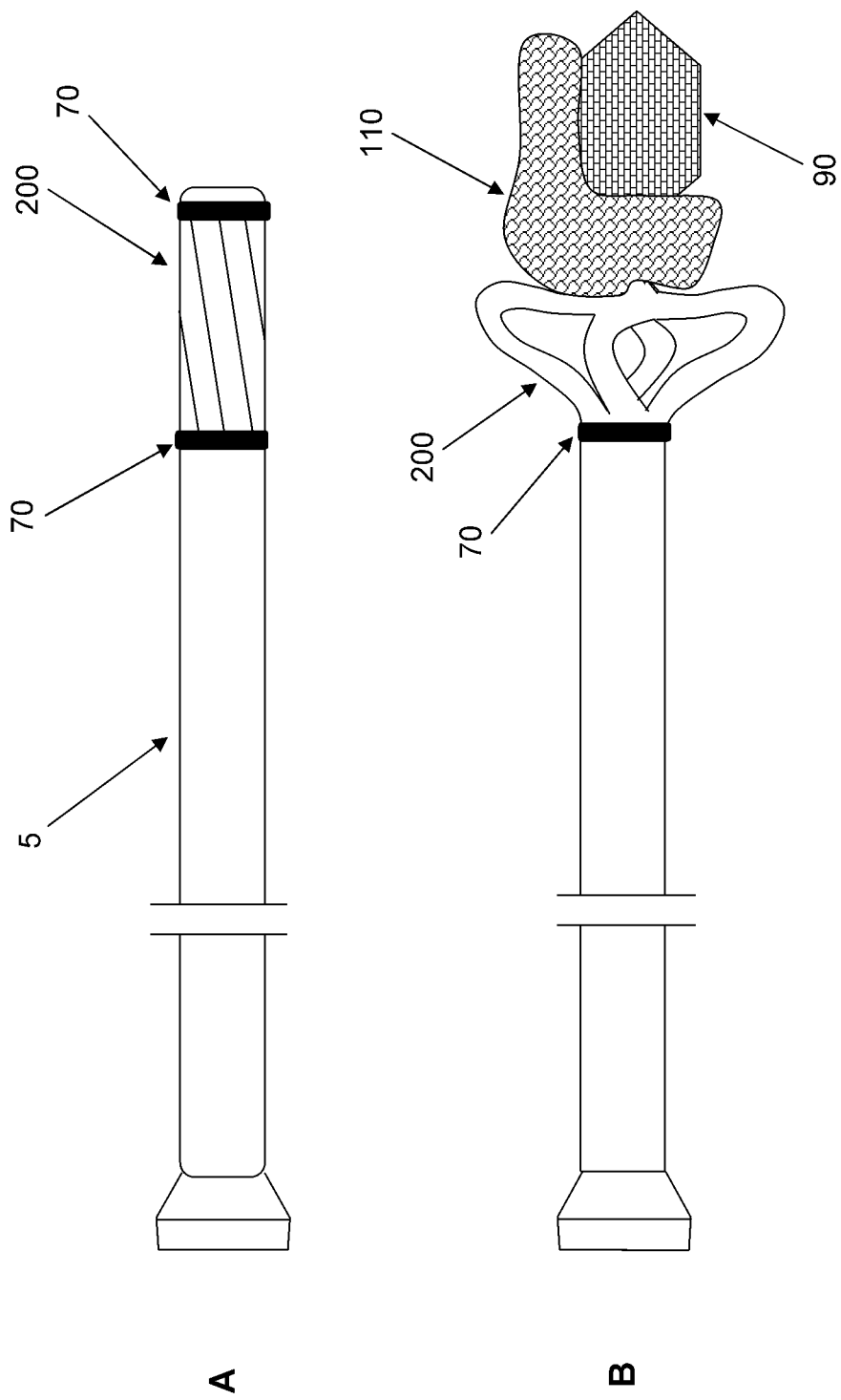
FIG. 20 shows a still another non-limiting illustrative embodiment of a device according to the invention where a microcatheter comprises a transformable tip at about its distal end.

FIG. 20 illustrates a further alternative of the embodiment in which the distal tip 200 of the microcatheter receives spiral cuts. Similar in the device of FIG. 19, the microcatheter's distal tip will be shaped into, e.g. a funnel form, when compressed during a retrieval procedure (FIG. 20B). In certain embodiments, the cutting process ends before reaching the very end of the microcatheter tip so that the very distal tip of the microcatheter is still closed.

Figure 21:
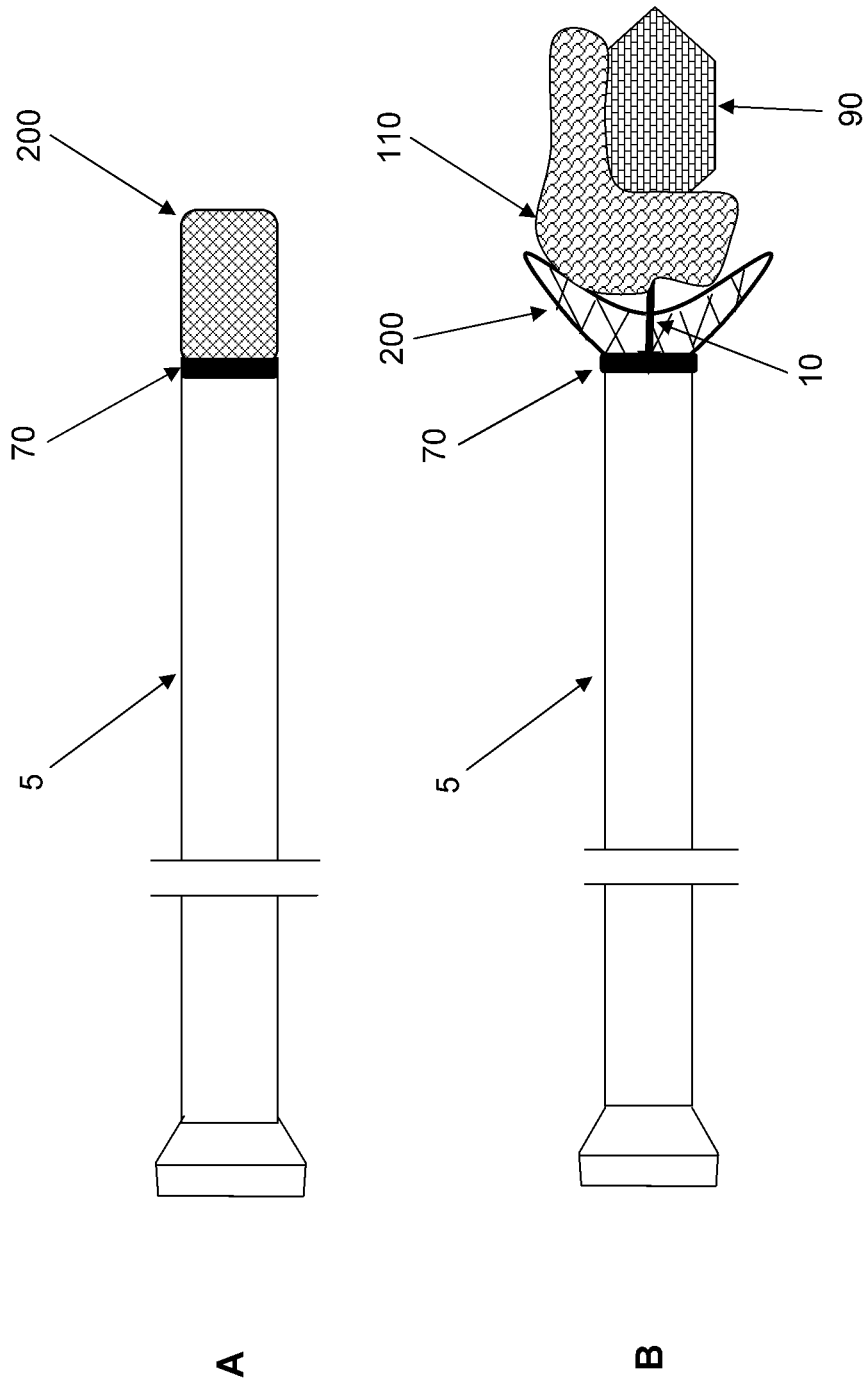
FIG. 21 shows a still another non-limiting illustrative embodiment of a device according to the invention where a microcatheter comprises a transformable tip at about its distal end.

FIG. 21 illustrates still another embodiment wherein the distal tip of the microcatheter is formed into a braid structure. Alternative, as described elsewhere in the application, a separate braid structure can be attached at the microcatheter's distal tip. The braid structure 200 that is attached at or formed in the microcatheter may be a metal braid with or without a plastic coating. Upon engaging a clot along with the distal engaging element 90, the braid structure 200 will be compressed and shaped into, e.g. a funnel form, so that the clot is held between the distal engaging element 90 and the braid structure 200.

Figure 22:
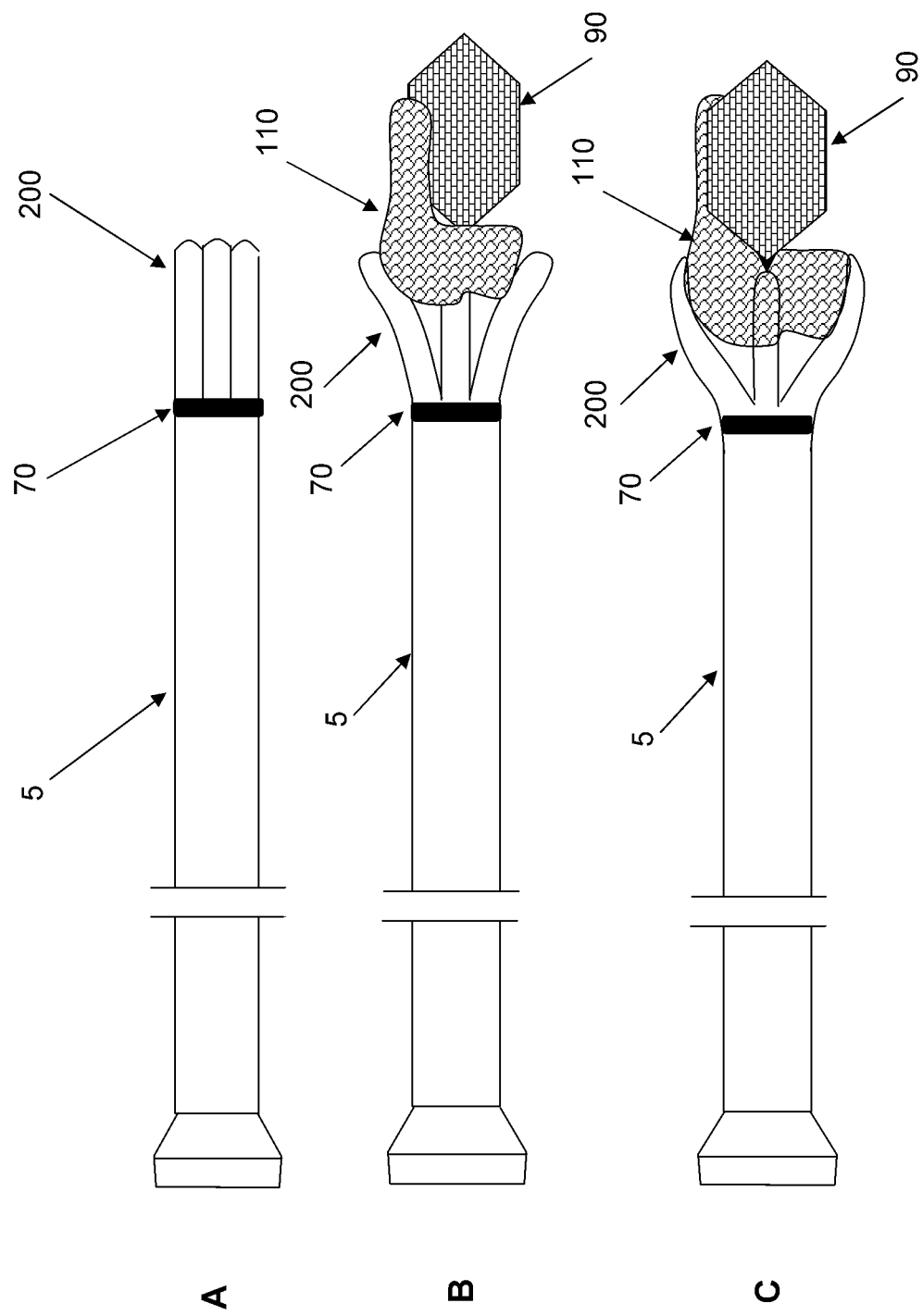
FIG. 22 shows still another non-limiting illustrative embodiment of a device according to the invention where a microcatheter comprises a transformable tip at about its distal end.

FIG. 22 illustrates still another embodiment wherein the cutting of the microcatheter's distal tip is through to the very end. Therefore, as seen in the figure, the very end of the microcatheter's distal tip is not closed. Upon pulling a clot backward with the distal engaging component 90, the tip of the microcatheter is compressed into, e.g. a funnel shape (spitted), and the clot is held between the distal engaging component 90 of the retrieval device and the distal tip of the microcatheter 200. FIGS. 22B and C show two different shapes of the opening tip of the microcatheter.

Figure 23:
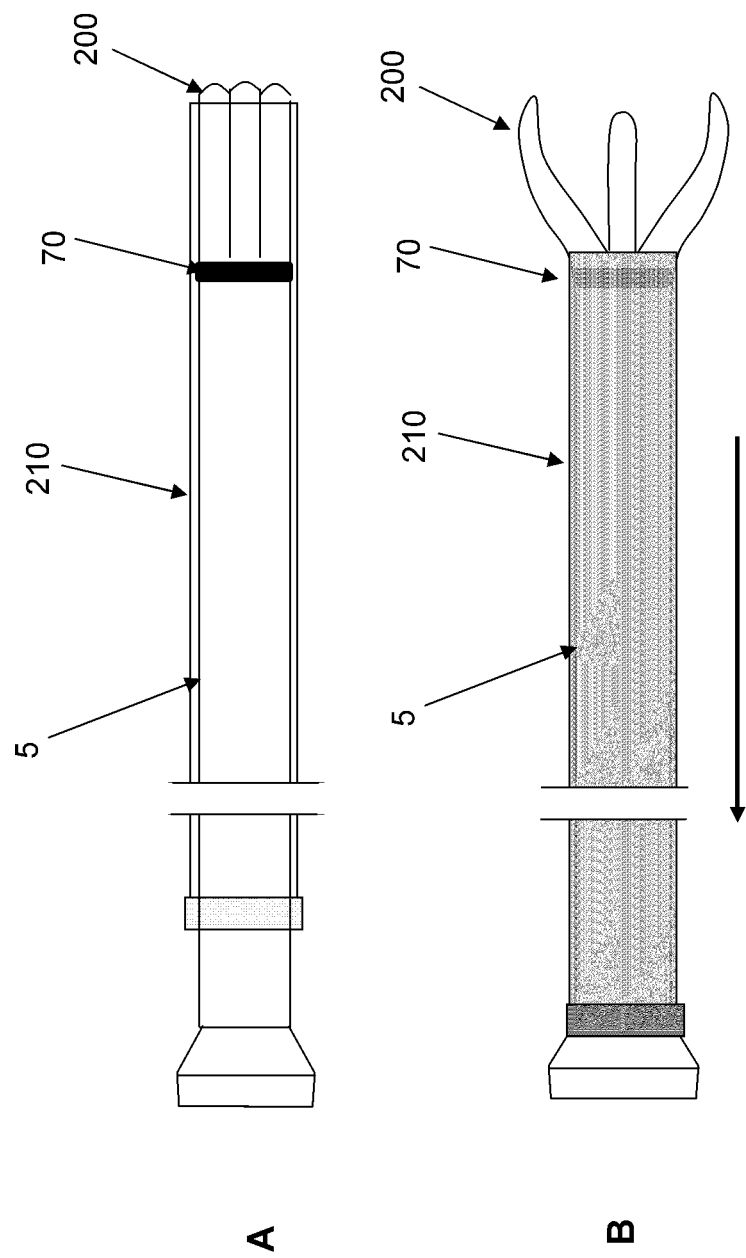
FIG. 23 shows still another non-limiting illustrative embodiment of a device according to the invention where a microcatheter comprises a transformable tip at about its distal end.

In certain embodiments, the proximal engaging element may comprise a portion of the distal end of the microcatheter comprising a microcather tip and a layer of thin tubing that covers the microcatheter tip. In some embodiments, at least part of the proximal engaging element is configured to change a shape when a layer of thin tubing is removed. An example of such embodiments is presented in FIG. 23. FIG. 23 illustrates a device in which a layer of outer sheath is applied to a microcatheter. In certain embodiments, a distal tip of the microcatheter used as an engaging element may comprise a pre-shaped structure or a shape-memory structure. The outer sheath 210 can hold the microcatheter's distal tip 200 so it can pass a clot prior to the engagement. When the microcatheter is pulled proximal to the clot, by pulling the outer sheath proximally, the tip opens to its pre-shaped, e.g. funnel shape. Alternatively, a shape-memory material can be used in the microcatheter's distal tip 200 so that it can form a certain shape when uncovered from the outer sheath.

Figure 24:
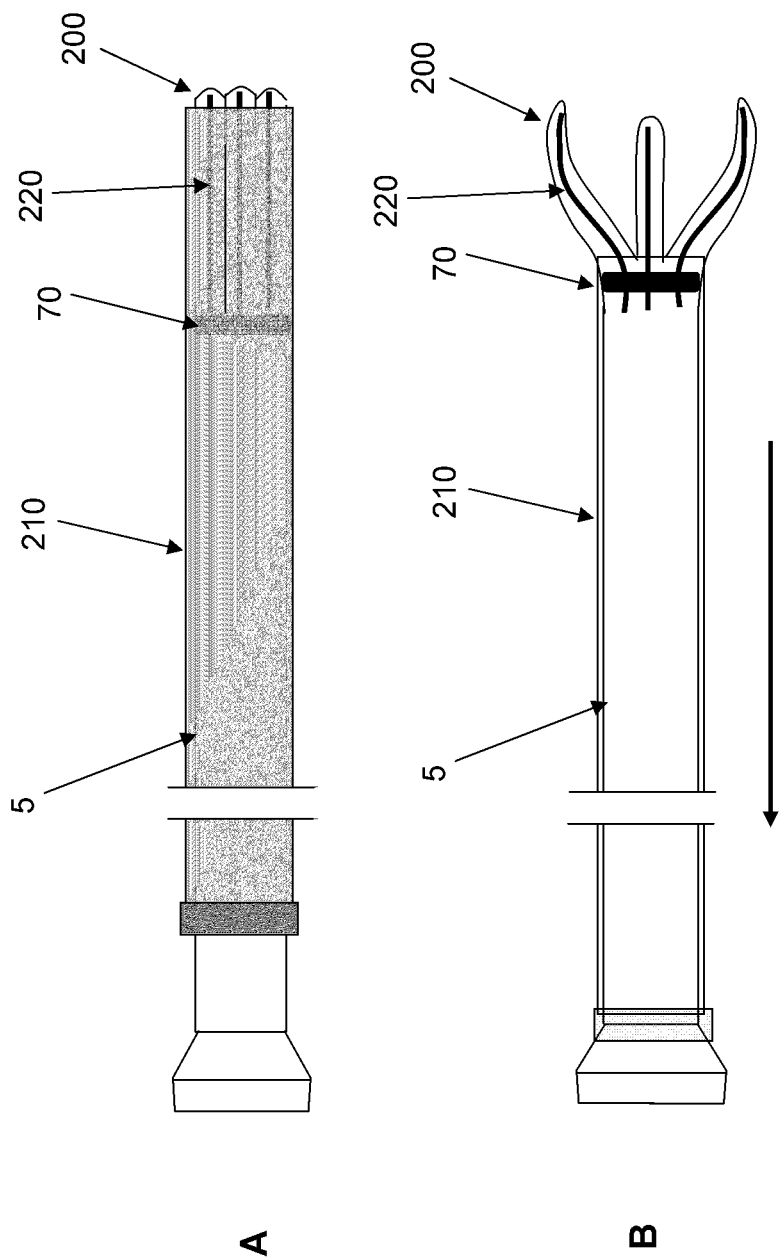
FIG. 24 shows still another non-limiting illustrative embodiment of a device according to the invention where a microcatheter comprises a transformable tip at about its distal end.

FIG. 24 illustrates still another embodiment of a device in which a wire is used to provide a certain shape at the microcatheter's distal tip. This design illustrated in FIG. 24B shows the microcatheter's distal tip 200 having a wire 220, e.g. an elastic wire, embedded in the tip to ensure that the tip will expand to its pre-set shape after being pulled out of the outer sheath 210.

Figure 25:
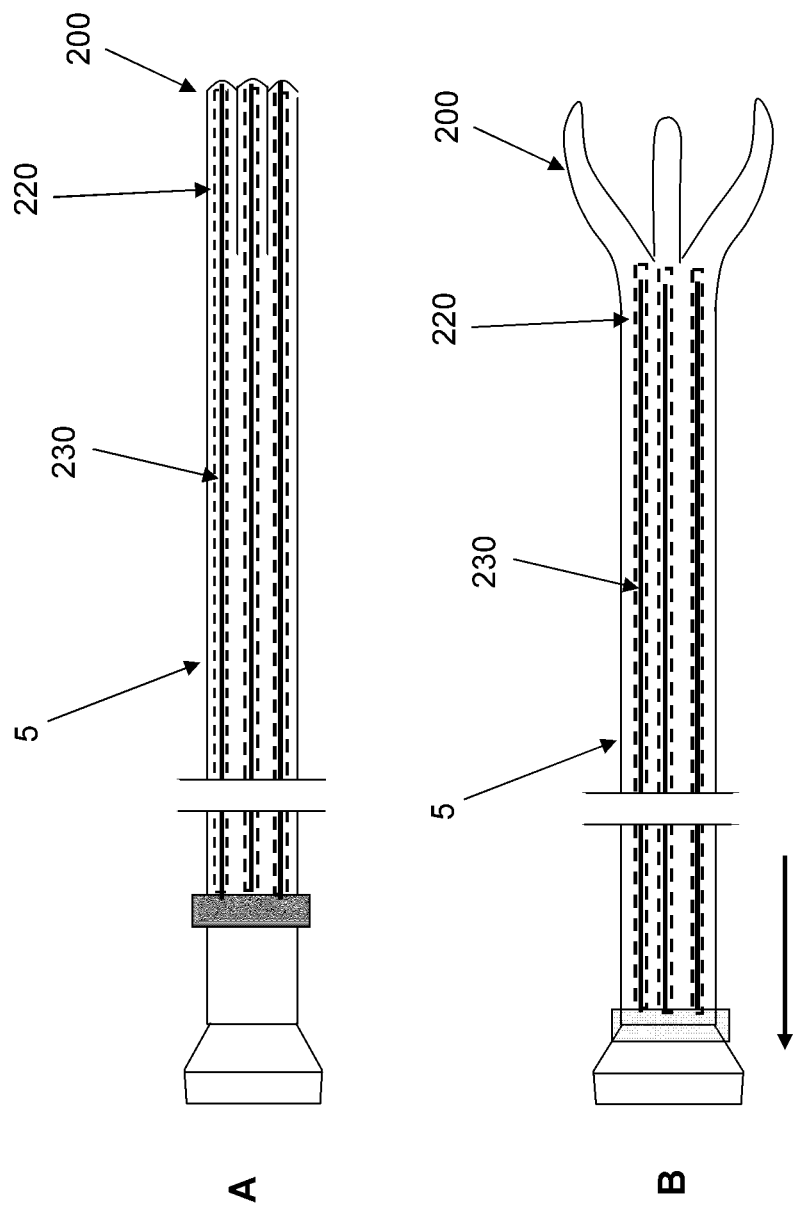
FIG. 25 shows still another non-limiting illustrative embodiment of a device according to the invention where a microcatheter comprises a transformable tip at about its distal end.

FIG. 25 illustrates still another embodiment of a device. In this particular embodiment, a pre-shaped funnel tip structure (sliced) is placed at the tip of a microcatheter, and the microcatheter's tip is held by wires 220 running through lumen(s) in the inner channel 230 of the microcatheter wall. The wires can hold the microcatheter's tip straight or unfolded until the tip passes the clot prior to the engagement. When the microcatheter is pulled proximal to the clot, by pulling the wires proximally, the tip opens to its pre-shaped, e. g. funnel shape.

Figure 26:
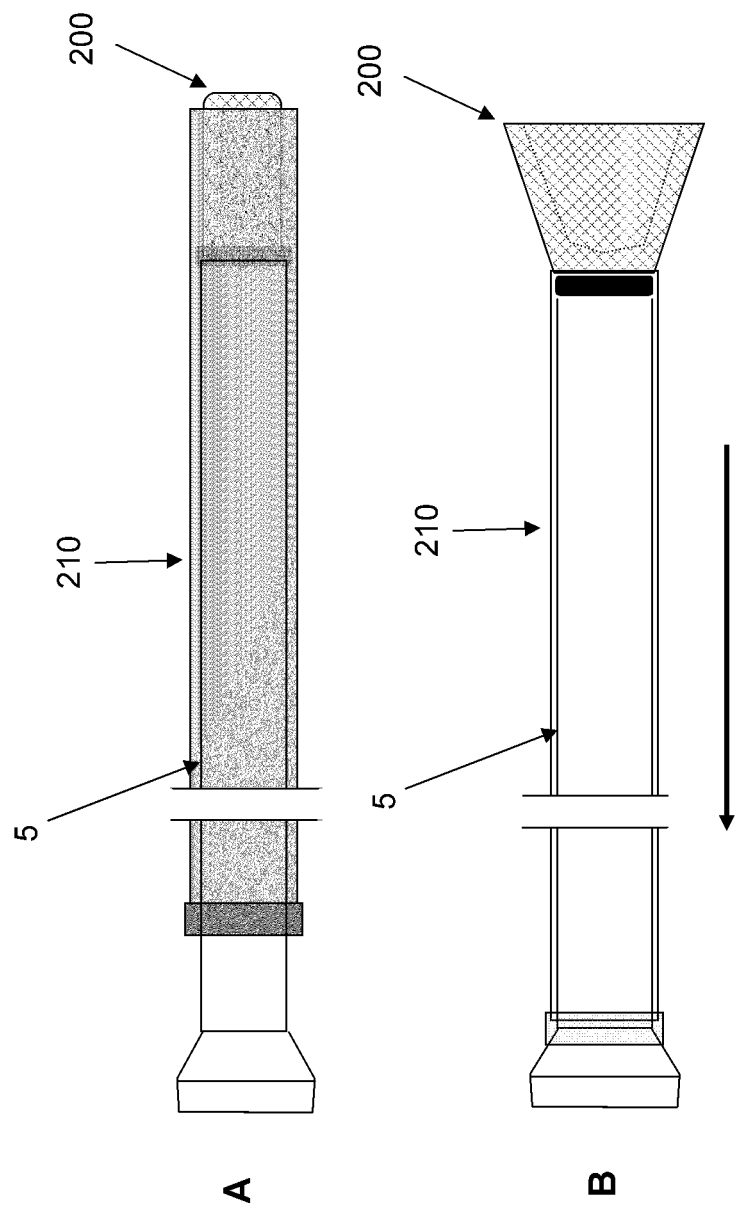
FIG. 26 shows still another non-limiting illustrative embodiment of a device according to the invention where a microcatheter comprises a transformable tip at about its distal end.

FIG. 26 illustrates still another embodiment of a device where a braid structure and an outer sheath are adopted together. A pre-shaped braid structure is placed at the microcatheter's distal tip, and a layer of an outer sheath holds the tip straight so the can be advanced in the circulation up to or through the clot prior to the engagement. When the microcatheter is—positioned proximal to clot, by pulling the outer sheath proximally, the braid tip opens to its pre-shaped, e.g. funnel shape.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A device for use in a blood vessel to remove an occlusion present in the blood vessel, the device comprising:
   a proximal end;
   a distal end;
   a handle at the proximal end of the device;
   a tubing compartment, which comprises a pusher tubing and a connecting tubing fixedly connected to each other;
   a central wire comprising a proximal end and a distal end thereof; and
   an engaging compartment at or near the distal end of the device, wherein the engaging compartment comprises:
      a proximal engaging element comprising a plurality of wires or struts, said proximal engaging element being open at a distal end of the proximal engaging element, wherein the proximal engaging element comprises a concave bend causing the distal end of the proximal engaging element to bend towards a central axis of the proximal engaging element such that the distal end points towards the central axis and the distal end is closer to the central axis than a part of the proximal engaging element proximal to the distal end; and
      a distal engaging element comprising a plurality of wires or struts forming a web or mesh, said distal engaging element being self-expandable, said distal engaging element being closed at a proximal end of the distal engaging element;
   wherein the proximal end of the distal engaging element fits inside the distal end of the proximal engaging element with room for a portion of the occlusion to fit therein, such that said portion of the occlusion can be captured between the proximal end of the distal engaging element and the distal end of the proximal engaging element when the distance between the distal engaging element and the proximal engaging element is shortened, wherein the proximal end of the distal engaging element is fixed at the distal end of the central wire, said central wire extending from the proximal end of the distal engaging element to the handle at the proximal end of the device, whereby the location of the distal engaging element in the blood vessel or its position with respect to the proximal engaging element is controlled by movement of the central wire and configured to be locked at the proximal end of the device once the occlusion is engaged; and wherein the distal engaging element is configured to hold the occlusion in all of the following ways:
(a) engaging the occlusion with a lateral side of the distal engaging element,
(b) frictionally engaging the occlusion between the lateral side of the distal engaging element and the wall of the blood vessel, and
(c) grabbing the occlusion between the proximal structure and the distal structure, while the device moves the occlusion within the blood vessel.

2. The device according to claim 1, wherein the proximal engaging element is an expandable element comprising a plurality of wires or struts and can expand into a funnel or cone shaped structure.

3. The device according to claim 1, wherein the proximal engaging element is associated with the central wire and moves along the central wire.

4. The device according to claim 1, wherein the proximal engaging element is fixed with the tubing compartment extending to a proximal end of the device, thereby a location of the proximal engaging element in the body lumen is controlled by movement of the tubing compartment.

5. The device according to claim 1, wherein the central wire comprises a wire, a cable, or a braid.

6. The device according to claim 1, wherein said distal end of the proximal engaging element is rounded or smoothed.

7. The device of claim 1, further comprising a microcatheter for delivery of the device.

* * * * *